US009809824B2

(12) United States Patent
Verthelyi et al.

(10) Patent No.: US 9,809,824 B2
(45) Date of Patent: Nov. 7, 2017

(54) CPG OLIGONUCLEOTIDE PRODRUGS, COMPOSITIONS THEREOF AND ASSOCIATED THERAPEUTIC METHODS

(75) Inventors: Daniela Verthelyi, Potomac, MD (US); Serge L. Beaucage, Silver Spring, MD (US); Andrzej Grajkowski, Kensington, MD (US)

(73) Assignee: The United States of America, Represented by the Secretary, Department of Health and Human Services, Washington, DC (US)

( * ) Notice: Subject to any disclaimer, the term of this patent is extended or adjusted under 35 U.S.C. 154(b) by 2416 days.

(21) Appl. No.: 11/721,409

(22) PCT Filed: Dec. 13, 2005

(86) PCT No.: PCT/US2005/044935
§ 371 (c)(1),
(2), (4) Date: Aug. 2, 2007

(87) PCT Pub. No.: WO2006/065751
PCT Pub. Date: Jun. 22, 2006

(65) Prior Publication Data
US 2009/0263405 A1    Oct. 22, 2009

Related U.S. Application Data

(60) Provisional application No. 60/635,744, filed on Dec. 13, 2004.

(51) Int. Cl.
*C07H 21/00* (2006.01)
*C12N 15/117* (2010.01)

(52) U.S. Cl.
CPC ........... *C12N 15/117* (2013.01); *C07H 21/00* (2013.01); *C12N 2310/17* (2013.01); *C12N 2310/315* (2013.01); *C12N 2310/351* (2013.01)

(58) Field of Classification Search
None
See application file for complete search history.

(56) References Cited

U.S. PATENT DOCUMENTS

| | | | |
|---|---|---|---|
| 3,534,017 A | 10/1970 | Fujimoto et al. |
| 4,415,732 A | 11/1983 | Caruthers et al. |
| 4,417,046 A | 11/1983 | Hsiung |
| 4,458,066 A | 7/1984 | Caruthers et al. |
| 4,469,863 A | 9/1984 | Ts'o et al. |
| 4,663,446 A | 5/1987 | Wright |
| 4,668,777 A | 5/1987 | Caruthers et al. |
| 4,725,677 A | 2/1988 | Köster et al. |
| 4,739,044 A | 4/1988 | Stabinsky |
| 4,757,141 A | 7/1988 | Fung et al. |
| 4,808,708 A | 2/1989 | Yoshida et al. |
| 4,816,569 A | 3/1989 | Miyoshi |
| 4,816,570 A | 3/1989 | Farquhar |
| 4,845,205 A | 7/1989 | Huynh Dinh et al. |
| 4,849,513 A | 7/1989 | Smith et al. |
| 4,950,745 A | 8/1990 | Ishido et al. |
| 4,973,679 A | 11/1990 | Caruthers et al. |
| 4,980,460 A | 12/1990 | Molko et al. |
| 5,023,243 A | 6/1991 | Tullis |
| 5,026,838 A | 6/1991 | Nojiri et al. |
| 5,039,796 A | 8/1991 | Engels et al. |
| 5,071,974 A | 12/1991 | Groody |
| 5,091,519 A | 2/1992 | Cruickshank |
| 5,134,228 A | 7/1992 | Takaku |
| RE34,069 E | 9/1992 | Köster et al. |
| 5,166,330 A | 11/1992 | Engels et al. |
| 5,212,304 A | 5/1993 | Fung et al. |
| 5,214,135 A | 5/1993 | Srivastava et al. |
| 5,252,760 A | 10/1993 | Urdea et al. |
| 5,258,538 A | 11/1993 | Fung et al. |
| 5,324,831 A | 6/1994 | Marquez et al. |
| 5,332,845 A | 7/1994 | Ueda et al. |
| 5,348,868 A | 9/1994 | Reddy et al. |
| 5,428,148 A | 6/1995 | Reddy et al. |
| 5,430,138 A | 7/1995 | Urdea et al. |
| 5,449,602 A | 9/1995 | Royer et al. |

(Continued)

FOREIGN PATENT DOCUMENTS

| | | |
|---|---|---|
| EP | 0 006 220 A1 | 1/1980 |
| EP | 0 090 789 A1 | 10/1983 |

(Continued)

OTHER PUBLICATIONS

Verthelyi et al. Immunoregulatory activity of CpG oligonucleotides in humans and non human primates. Clinical Immunology, 2003, vol. 109, 64-71.*
Verthelyi et al (Journal of Immunology, 166:2372-2377, 2001).*
Alama et al., "Antisense Oligonucleotides as Therapeutic Agents," *Pharmacol. Res.*, 36(3), 171-178 (1997).
Barone et al., "In Situ Activation of Bis-Dialkylaminophosphines—A New Method for Synthesizing Deoxyoligonucleotides on Polymer Supports," *Nucl. Acids Res.*, 12(10), 4051-4061 (1984).
Beaucage et al., "An Improved Sulfurization Reagent for the Synthesis of Sulfur-Containing Oligonucleotides," *Ann. New York Acad. Sci.*, 616, 483-485 (1990).
Beaucage et al., "Synthetic Strategies and Parameters Involved in the Synthesis of Oligodeoxyribonucleotides According to the Phosphoramidite Method," *Current Protocols in Nucleic Acid Chemistry*, 1, 3.3.1-3.3.20 (2000).

(Continued)

*Primary Examiner* — Patricia Duffy
(74) *Attorney, Agent, or Firm* — Klarquist Sparkman, LLP

(57) ABSTRACT

The present invention provides a CpG oligonucleotide prodrug that includes a thermolabile substituent on at least one nucleotide thereof. The present invention also provides compositions that include a carrier and a therapeutically effective amount of at least one CpG oligonucleotide prodrug. The present invention further provides therapeutic methods of using such thermolabile CpG oligonucleotide prodrugs and compositions thereof. The present invention further provides a method of inhibiting tetrad formation in a CpG oligonucleotide by functionalizing the CpG oligonucleotide with one or more thermolabile substituents.

25 Claims, 10 Drawing Sheets

(56) References Cited

U.S. PATENT DOCUMENTS

| | | |
|---|---|---|
| 5,506,351 A | 4/1996 | McGee |
| 5,510,476 A | 4/1996 | Ravikumar et al. |
| 5,518,651 A | 5/1996 | Reddy et al. |
| 5,519,126 A | 5/1996 | Hecht |
| 5,525,719 A | 6/1996 | Srivastava et al. |
| 5,550,098 A | 8/1996 | Aso et al. |
| 5,556,961 A | 9/1996 | Foote et al. |
| 5,571,902 A | 11/1996 | Ravikumar et al. |
| 5,574,146 A | 11/1996 | Reddy et al. |
| 5,614,622 A | 3/1997 | Iyer et al. |
| 5,616,700 A | 4/1997 | Reddy et al. |
| 5,623,068 A | 4/1997 | Reddy et al. |
| 5,639,867 A | 6/1997 | Brill |
| 5,645,985 A | 7/1997 | Froehler et al. |
| 5,646,265 A | 7/1997 | McGee |
| 5,652,358 A | 7/1997 | Pfleiderer et al. |
| 5,663,153 A | 9/1997 | Hutcherson et al. |
| 5,670,489 A | 9/1997 | Baxter et al. |
| 5,681,940 A | 10/1997 | Wang et al. |
| 5,700,919 A | 12/1997 | Seliger et al. |
| 5,703,218 A | 12/1997 | Urdea et al. |
| 5,703,223 A | 12/1997 | Wickstrom et al. |
| 5,705,621 A | 1/1998 | Ravikumar |
| 5,712,378 A | 1/1998 | Wang |
| 5,714,597 A | 2/1998 | Ravikumar et al. |
| 5,731,429 A | 3/1998 | Reddy et al. |
| 5,763,599 A | 6/1998 | Pfleiderer et al. |
| 5,866,700 A | 2/1999 | Pfleiderer et al. |
| 5,889,165 A | 3/1999 | Fodor et al. |
| 5,908,926 A | 6/1999 | Pirrung et al. |
| 5,959,099 A | 9/1999 | Cheruvallath et al. |
| 6,001,982 A | 12/1999 | Ravikumar et al. |
| 6,022,963 A | 2/2000 | McGall et al. |
| 6,043,060 A | 3/2000 | Imanishi |
| 6,194,388 B1 | 2/2001 | Krieg et al. |
| 6,207,646 B1 | 3/2001 | Krieg et al. |
| 6,239,116 B1 | 5/2001 | Krieg et al. |
| 6,339,068 B1 | 1/2002 | Krieg et al. |
| 6,406,705 B1 | 6/2002 | Davis et al. |
| 6,429,199 B1 | 8/2002 | Krieg et al. |
| 6,653,292 B1 | 11/2003 | Krieg et al. |
| 6,727,230 B1 | 4/2004 | Hutcherson et al. |
| 6,762,298 B2 | 7/2004 | Beaucage et al. |
| 2001/0044529 A1 | 11/2001 | Beaucage et al. |
| 2003/0060440 A1 | 3/2003 | Klinman et al. |
| 2003/0144229 A1 | 7/2003 | Klinman et al. |
| 2004/0105872 A1 | 6/2004 | Klinman et al. |
| 2004/0241841 A1 | 12/2004 | Klinman et al. |
| 2004/0248834 A1 | 12/2004 | Klinman et al. |
| 2005/0020827 A1 | 1/2005 | Beaucage et al. |
| 2005/0209184 A1 | 9/2005 | Klinman et al. |
| 2006/0019239 A1 | 1/2006 | Ivins et al. |
| 2006/0074039 A1 | 4/2006 | Klinman et al. |
| 2006/0281911 A1 | 12/2006 | Beaucage et al. |

FOREIGN PATENT DOCUMENTS

| | | |
|---|---|---|
| EP | 0 092 574 B1 | 11/1983 |
| EP | 0 196 101 A2 | 10/1986 |
| EP | 0 219 342 A2 | 4/1987 |
| EP | 0 241 363 A1 | 10/1987 |
| EP | 0 323 152 A2 | 7/1989 |
| GB | 2 153 356 A | 8/1985 |
| WO | 88/02004 A1 | 3/1988 |
| WO | 93/12132 A1 | 6/1993 |
| WO | 95/26204 A1 | 10/1995 |
| WO | 96/02555 A1 | 2/1996 |
| WO | 96/29337 A1 | 9/1996 |
| WO | 97/47637 A1 | 12/1997 |
| WO | 98/07734 A1 | 2/1998 |
| WO | 98/11211 A2 | 3/1998 |
| WO | 98/18810 A1 | 5/1998 |
| WO | 98/37919 A1 | 9/1998 |
| WO | 98/40100 A1 | 9/1998 |
| WO | 98/52581 A1 | 11/1998 |
| WO | 00/56749 A1 | 9/2000 |
| WO | WO 00/56749 * | 9/2000 |
| WO | 00/61151 A2 | 10/2000 |
| WO | 01/51500 A1 | 7/2001 |
| WO | 03/020884 A2 | 3/2003 |
| WO | 03/027313 A2 | 4/2003 |
| WO | WO 03/027313 * | 4/2003 |
| WO | 03/048179 A2 | 6/2003 |
| WO | 2004/012669 A2 | 2/2004 |
| WO | 2004/098491 A2 | 11/2004 |
| WO | 2004/101582 A2 | 11/2004 |
| WO | WO 2004/101582 * | 11/2004 |
| WO | 2006/065751 A2 | 6/2006 |

OTHER PUBLICATIONS

Beaucage et al., "Advances in the Synthesis of Oligonucleotides by the Phosphoramidite Approach," *Tetrahedron*, 48(12), 2223-2311 (1992).

Beaucage et al., "The Synthesis of Modified Oligonucleotides by the Phosphoramidite Approach and Their Applications," *Tetrahedron*, 49(28), 6123-6194 (1993).

Beaucage, "Oligodeoxyribonucleotides Synthesis," *Methods in Molecular Biology*, 20, 33-61 (1993).

Bigg et al., "Triethylamine/Aluminum Chloride Promoted Aminolysis of Lactones: A Useful Method for the Preparation of Omega-Hydroxyalkanamides," *Synthesis*, 277-278 (Mar. 1992).

Boal et al., "Cleavage of Oligodeoxyribonucleotides From Controlled-Pore Glass Supports and Their Rapid Deprotection by Gaseous Amines," *Nucl. Acids Res.*, 24(15), 3115-3117 (1996).

Brown et al., "A New Base-Stable Linker for Solid-Phase Oligonucleotide Synthesis," *J. Chem. Soc. Chem. Commun.*, 891-893 (1989).

Cao et al., "A Novel Route for Solid Phase Synthesis of Polynucleotides Using Phosphite Chemistry," *Tetrahedron Letters*, 24(10), 1019-1020 (1983).

Chmielewski et al., "Thermolytic Carbonates for Potential 5'-Hydroxyl Protection of Deoxyribonucleosides," *J. Org. Chem.*, 68(26), 10003-10012 (2003).

Cieslak et al., "Thermolytic Properties of 3-(2-Pyridyl)-1-Propyl and 2-[N-Methyl-N- (2-Pyridyl)]Aminoethyl Phosphate/Thiophosphate Protecting Groups in Solid-Phase Synthesis of OligodeoxyribonucleotideS." *J. Org. Chem.*, 69(7), 2509-2515, (2004).

Cieslak et al., "Thermolytic 4-Methylthio-1-Butyl Group for Phosphate/Thiophosphate Protection in Solid-Phase Synthesis of DNA Oligonucleotides," *J. Org. Chem.*, 68(26), 10123-10129 (2003).

Elkins et al., "Bacterial DNA Containing CpG Motifs Stimulates Lymphocyte- Dependent Protection of Mice Against Lethal Infection With Intracellular Bacteria," *J. Immun.*, 162, 2291-2298 (1999).

Finger et al., "Aromatic Fluorine Compounds. IX. 2-Fluoropyridines," *J. Am. Chem. Soc.*, 81 (10), 2674-2675 (1959).

Gardrat et al., "A New Synthesis of DL-5-Vinyloxazolidine-2-Thione, A Natural Antithyroid Factor," *J. Heterocyclic Chem.*, 27, 811-812 (1990).

Grajkowski et al., "Conceptual "Heat-Driven" Approach to the Synthesis of DNA Oligonucleotides on Microarrays," *Annals N. Y. Academy Sciences*, 1002, 1-11 (2003).

Grajkowski et al., "Thermolytic CpG-Containing DNA Oligonucleotides as Potential Immunotherapeutic Prodrugs," *Nucleic Acids Res.*, 33, 3550-3560 (2005).

Grajkowski et al., "The 2-(N-Formyl-N-Methyl)Aminoethyl Group as a Potential Phosphate/Thiophosphate Protecting Group in Solid-Phase Oligodeoxyribonucleotide Synthesis," *Organic Letters*, 3(9), 1287-1290 (2001).

Gray et al., "Aminopyridines. II. The Preparation and Properties of 2- (Hydroxyalkylamino)Pyridines," *J. Am. Chem. Soc.*, 81, 4351-4355 (1959).

Gursel et al., "CpG Oligodeoxyucleotides Induce Human Monocytes to Mature Into Functional Dendritic Cells," *Eur.J. Immunol.*, 32, 2617-2622 (2002).

(56) References Cited

OTHER PUBLICATIONS

Gursel et al., "Differential and Competitive Activation of Human Immune Cells by Distinct Classes of CpG Oligodeoxynucleotide," *J. Leukocyte Biology*, 71, 813-820 (2002).
Guzaev et al., "A Novel Phosphate Protection for Oligonucleotide Synthesis: The 2- [(1-Naphthyl)Carbamoyloxy]Ethyl (NCE) Group," *Tetrahedron Letters*, 41, 5623-5626 (2000).
Halperin et al., "A Phase I Study of the Safety and Immunogenicity of Recombinant Hepatisis B Surface Antigen Co-Administered With an Immunostimulatory Phosphorothioate Oligonucleotide Adjuvant," *Vaccine*, 21, 2461-2467 (2003).
Hartmann et al., "Rational Design of New CpG Oligonucleotides That Combine B Cell Activation With High IFN-Alpha Induction in Plasmacytoid Dendritic Cells," *Eur. J. Immunol.*, 33, 1633-1641 (2003).
Iyer et al., "The Automated Synthesis of Sulfur-Containing Oligodeoxyribonucleotides Using 3H-1,2-Benzodithiol-3-One 1,1-Dioxide as a Sulfur-Transfer Reagent," *J. Org. Chem.*, 55(15), 4693-4699 (1990).
Iyer et al., "Nucleoside Oxazaphospholidines as Novel Synthons in Oligonucleotide Synthesis," *J. Org. Chem.*, 60, 5388-5389 (1995).
Iyer et al., "A Novel Nucleoside Phosphoramidite Synthon Derived From 1r, 2s- Ephedrine," *Tetrahedron: Asymmetry*, 6(5), 1051-1054 (1995).
Iyer, "Nucleobase Protection of Deoxyribo- and Ribonucleosides," *Current Protocols in Nucleic Acid Chemistry*, 1, 2.1.1-2.1.17 (2000).
Kawanobe et al., "Peptide Synthesis by Using N-Acylphosphoramidites," *Chemistry Letters, Chem. Soc. of Japan*, 825-828 (1982).
Klinman et al., "CpG DNA: Recognition by and Activation of Monocytes," *Microbes and Infection*, 4, 897-901 (2002).
Klinman et al., "CpG Motifs as Immune Adjuvants," *Vaccine*, 17, 19-25 (1999).
Klinman et al.,"Immune Recognition of Foreign DNA: A Cure for Bioterrorism?," *Immunity*, 11, 123-129 (1999).
Klinman et al., "CpG Motifs Present in Bacterial DNA Rapidly Induce Lymphocytes to Secrete Interleukin 6, Interleukin 12, and Interferon Gamma," *Proc. Natl. Acad. Sci. USA*, 93, 2879-2883 (1996).
Klinman, "Immunotherapeutic Uses of CpG Oligodeoxynucleotides," *Nature Reviews: Immunology*, 4, 1-10 (2004).
Klinman, "Use of CpG Oligodeoxynucleotides as Immunoprotective Agents," *Expert Opin. Biol. Ther.* 4(6), 937-946 (2004).
Krieg et al., "CpG Motifs in Bactrial DNA Trigger Direct B-Cell Activation," *Nature*, 374, 546-549 (1995).
Lefebvre et al., "Mononucleoside Phosphotriester Derivatives With S-Acyl-2-Thioethyl Bioreversible Phosphate-Protecting Groups: Intracellular Delivery of 3'- Azido-2'-3'-Dideoxythymidine 5'-Monophosphate," *J. Med. Chem.*, 38(2), 3941-3950 (1995).
Liang et al., "Activation of Human B Cells by Phosphorothioate Oligodeoxynucleotides," *J. Clin. Invest.*, 98, 1119-1129 (1996).
Lonnberg et al., "Towards Genomic Drug Therapy With Antisense Oligonucleotides," *Ann. Med.*, 28, 511-522 (1996).
Maniatis et al., *Molecular Cloning: A Laboratories Manual*, 173-185, Cold Spring Harbor Laboratory Press, Woodbury, NY (1982).
Martin, "Ein Neuer Zugang Zu 2'-O-Alkylribonucleosiden Und Digenschaften Deren Oligonucleotide," *Helv. Chim. Acta.*, 78, 486-504 (1995).
McBride et al., "Amidine Protecting Groups for Oligonucleotide Synthesis," *J. Am. Chem. Soc.*, 108, 2040-2048 (1986).
McCluskie et al., "Cutting Edge: CpG DNA is a Potent Enhancer of Systemic and Mucosal Immune Responses Against Hepatitis B Surface Antigen With Intranasal Administration to Mice," *J. Immun.*, 161, 4463-4466 (1998).
Mendez et al., "Coinjection With CpG-Containing Immunosimulatory Oligonucleotides Reduces the Pathogenicity of a Live Vaccine Against Cutaneous Leishmaniasis but Maintains Its Potency and Durability," *Infect. & Immun.*, 71(9), 5121-5129 (2003).
Mizrakh et al., "3-Acyl-1,3,2-Oxazaphospholanes and Phosphorinanes. Synthesis and Certain Properties," *Chemical Abstracts*, 83(23), 454 (1975).
Mizrakh et al., "Reactions of Alikyl Tetraalkylphosphorodiamidites With N-(2-Hydroxyethyl)Acetamide," *Zh. Obs. Khim.*, 45(10), 2343-2344 (1975).
Mizrakh et al., "Thermal Decomposition of 2-(2-Acetamidoethoxy)- and 2-(3- Acetamidopropoxy)-1,3,2-Dioxaphospholanes," *Zh. Obs. Khim.*, 45(3), 549-552 (1975).
Mizrakh et al., "3-Acyl-1,3,2-Oxazaphospholanes and Phosphorinanes. Synthesis and Certain Properties," *Zh. Obs. Khim.*, 45(7), 1469-1473 (1975).
Murphy et al., "Intramolecular Free-Radical Substitution of Pyridinium Rings," *Tetrahedron*, 47(24), 4077-4088 (1991).
Online News Article, "Coley Pharmaceutical Group Initiates Phase I/II Clinical Trial of CpG 7909 in Melanoma Patients," Coley Pharmaceutical Group, Inc., http://www.coleypharma.com/coley/pr_1025200219 (2002).
Online News Article, "Coley Pharmaceutical Group Receives Ninth U.S. Patent," *Canada News Wire*, http://www.vaccinationnews.com/dailynews/July2002/ColeyPharma9.htm (2002).
Online News Article, "Coley Pharmaceutical Group Receives Patent for Dendritic Cell Activation," Coley Pharmaceutical Group, Inc., http://www.investinbiotech.com/pressroom_release.php?id=732. (2002).
Prakash et al., "2'-O-{2-[N,N-(Dialkyl)Aminooxy]Ethyl}-Modified Antisense Oligonucleotides," *Org. Lett.*, 2(25), 3995-3998 (2000).
Probst et al., "Homo- Und Copolymerisation Von N,N-Disubstituierten Carbamoylalkylacrylaten Und —Methacrylaten," *Makromol. Chem.*, 177, 2681-2695 (1976).
Pudovik et al., "N-Acylated Aminophospholanes," *Chemical Abstracts*, 79(11), 441 (1973).
Pudovik et al., "N-Acetylated 1,3,2-Oxaazaphospholanes," *Chemical Abstracts*, 81(11), 484 (1974).
Regan et al., "Large-Scale Preparation of the Sulfur Transfer Reagent 3H-1,2-Benzodithio1-3-One 1,1-Dioxide," *Org. Prep. Proc. Int.*, 24(4), 488-492 (1992).
Saegusa et al., "Kinetics and Mechanism of the Isomerization Polymerization of 2- Methyl-2-Oxazoline by Benzyl Chloride and Bromide Initiators. Effect of Halogen Counteranions," *Makromol. Chem.*, 177, 2271-2283 (1976).
Scanlon et al., "Oligonucleotide-Mediated Modulation of Mammalian Gene Expression," *FASEB J.*, 9, 1288-1296 (1995).
Scremin et al., "Stepwise Regeneration and Recovery of Deoxyribonucleoside Phosphoramidite Monomers During Solid-Phase Oligonucleotide Synthesis," *J. Org. Chem.*, 59(8), 1963-1966 (1994).
Shibanuma et al., "Synthesis of the Metabolites of 2-(N-Benzyl-N-Methylamino)Ethyl Methyl 2,6-Dimethyl-4-(m-Nitrophenyl)-1,4-Dihydropyridine-3,5-Dicarboxylate Hydrochloride (Nicardipine Hydrochloride, Yc-93)" *Chem. Pharm. Bull.*, 28(9), 2609-2613 (1980).
Smith et al., "Oligonucleotide Labeling Methods 4. Direct Labeling Reagents With a Novel, Non-Nucleosidic, Chirally Defined 2-Deoxy-Beta-D-Ribosyl Backbone," *Nucleosides & Nucleotides*, 15(10), 1581-1594 (1996).
Somei et al., "Titanium (III) Chloride for the Reduction of Heteroaromatic and Aromatic Nitro Compounds," *Chem. Pharm. Bull.*, 28(8), 2515-2518 (1980).
Stec et al., "Novel Route to Oligo(Deoxyribonucleoside Phosphorothioates). Stereocontrolled Synthesis of P-Chiral Oligo(Deoxyribonucleoside Phosphorothioates)," *Nucleic Acids Res.*, 19(21), 5883-5888 (1991).
Tsuruoka et al., "Selective and Facile 5'-De(Thio)Phosphorylation of Oligonucleotides Having a 5'-Terminal Phosphorothioate Group by Simple Thermolysis," *Tetrahedron Letters*, 40, 8411-8414 (1999).
Verthelyi et al., "CpG Oligodeoxynucleotides as Vaccine Adjuvants in Primates," *J. Immun.*, 168, 1659-1663 (2002).

(56) References Cited

OTHER PUBLICATIONS

Verthelyi et al., "CpG Oligodeoxynucleotides Improve the Response to Hepatitis B Immunization in Healthy and Siv-Infected Rhesus Macaques," *AIDS*, 18, 1003-1008 (2004).
Verthelyi et al., "Differential Signaling by CpG DNA in DCS and B Cells: Not Just Tlr9," *Trends Immunol.*, 24(10), 519-522 (2003).
Verthelyi et al., "Immuoregulatory Activity of CpG Oligonucleotides in Humans and Nonhuman Primates," *Clinical Immunology*, 109, 64-71 (2003).
Verthelyi et al., "Diassociation of Sex Hormone Levels and Cytokine Production in SLE Patients," *Lupus*, 10, 352-358 (2001).
Verthelyi et al., "Estrogen Increases the Number of Plasma Cells and Enhances Their Autoantibody Production in Nonautoimmune C57bl/6 Mice," *Cellular Immunology*, 189,125-134 (1998).
Verthelyi et al., "Human Peripheral Blood Cells Differentially Recognize and Respond to Two Distinct CpG Motifs," *J. Immunol.*, 166, 2372-2377 (2001).
Vollmer et al., "Immunopharmacology of CpG Oligodeoxynucleotides and Ribavarin," *Antimicrobial Agents and Chemotherapy*, 48(6), 2314-2317 (2004).
Waldner et al., "Hydrophobic Effects in Duplexes With Modified Oligonucleotide Backbones and RNA," *Bioorg. Med. Chem. Letters*, 6(19), 9, 2363-2366 (1996).
Wang et al., "A Stereoselective Synthesis of Dinucleotide Phosphorothioates, Using Chiral Indol-Oxazaphosphorine Intermediates," *Tetrahedron Letters*, 38(22), 3797-3800 (1997).
Weiner et al., "N-2-Pyridylalkanolamines and Esters," *J. Org. Chem.*, 14, 868-872 (1949).
Wilk et al., "Deoxyribonucleoside Cyclic N-Acylphosphoramidites as a New Class of Monomers for the Stereocontrolled Synthesis of Oligothymidylyl- and Oligodeoxycytidylyl-Phosphorothioates," *J. Am. Chem. Soc.*, 122, 2149-2156 (2000).
Wilk et al., "N-Trifluoroacetylamino Alcohols as Phosphodiester Protecting Groups in the Synthesis of Oligodeoxyribonucleotides," *J. Org. Chem.*, 62(20), 6712-6713 (1997).
Wilk et al., "The 4-[N-Methyl-N-(2,2,2-Trifluoroacetyl)Amino]Butyl Group as an Alternative to the 2-Cyanoethyl Group for Phosphate Protection in the Synthesis of Oligodeoxyribonucleotides," *J. Org. Chem.*, 64(20), 7515-7522 (1999).
Wilk et al., "The 3-(N-Tert-Butylcarboxamido)-1-Propyl Group as an Attractive Phosphate/Thiophosphate Protecting Group for Solid-Phase Oligodeoxyribonucleotide Synthesis," *J. Org. Chem.*, 67, 6430-6438 (2002).
Wilk et al., "The 4-Oxopentyl Group as a Labile Phosphate/Thiophosphate Protecting Group for Synthetic Oligodeoxyribonucleotides," *Tetrahedron Letters*, 42, 5635-5639 (2001).
Wilk et al.; "Deoxyribonucleoside Cyclic N-Acylphosphoramidites as a New Class of Monomers for the Stereocontrolled Synthesis of Oligothymidylyl- and Oligodeoxycytidylyl-Phosphorothioates," *J. Am. Chem. Soc.*, 122, 2149-2156 (2000).
Wilk et al.; "The 3-(N-Tert-Butylcarboxamido)-1-Propyl Group as an Attractive Phosphate/Thiophosphate Protecting Group for Solid-Phase Oligodeoxyribonucleotide Synthesis," *J. Org. Chem.*, 67, 6430-6438 (2002).
Wincott, "Strategies for Oligoribonucleotide Synthesis According to the Phosphoramidite Method," *Current Protocols in Nucleic Acid Chemistry*, 1, 3.5.1-3.5.12 (2001).
Yang et al., "1,3,2-Oxazaphospholidine Derivatives. II. Synthesis and Properties of 2-Diethylamino 3-Substituted Formul-1,3,2-Oxazaphospholidines," *Chem. Abs.*, 111, 97382x (1989).
Yi et al., "Rapid Immune Activation by CpG Motifs in Bacterial DNA—Systemic Induction of IL-6 Transcription Through an Antioxidant-Sensitive Pathway," *J. Immun.*, 157, 5394-5402 (1996).
Zeuner et al., "Influence of Stimulatory and Suppressive DNA Motifs on Host Susceptibility to Inflammatory Arthritis," *Arthritis & Rheumatism*, 48(6), 1701-1707 (2003).
Zeuner et al., "Response of Peripheral Blood Mononuclear Cells From Lupus Patients to Stimulation by CpG Oligodeoxynucleotides," *Rheumatology*, 42, 1-7 (2003).
Zhang et al., "NMR of Organophosphorous Compounds. VI. 13C NMR of 1,3,2-Oxazaphospholidine Derivatives," *Chem. Abs.*, 126(2), 18939t (1997).
Zimmerman et al., "Immunostimulatory DNA as Adjuvant: Efficacy of Phosphodiester CpG Oligonucleotides is Enhanced by 3' Sequence Modifications," *Vaccine*, 21(9-10), 990-995 (2003).

* cited by examiner

B: a, thymin-1yl; b, $N^4$-benzoylcytosin-1-yl;
c, $N^6$-benzoyladenin-9-yl; d, $N^2$-isobutyrylguanin-9-yl $B_n$ = thymin-1-yl, cytosin-1-yl, adenin-9-yl or guanin-9-yl $G_{ps}C_{ps}T_{ps}A_{ps}G_{ps}A_{ps}C_{ps}G_{ps}T_{ps}T_{ps}A_{ps}G_{ps}C_{ps}G_{ps}T$

FIG. 8

$G_{PS(FMA)}C_{PS(FMA)}T_{PS(FMA)}A_{PS(FMA)}G_{PS(FMA)}A_{PS(FMA)}C_{PS(FMA)}G_{PS(FMA)}T_{PS(FMA)}T_{PS(FMA)}A_{PS(FMA)}G$ $_{PS(FMA)}C_{PS(FMA)}G_{PS(FMA)}T$

FIG. 9

CPG OLIGONUCLEOTIDE PRODRUGS, COMPOSITIONS THEREOF AND ASSOCIATED THERAPEUTIC METHODS

CROSS-REFERENCE TO RELATED APPLICATIONS

This application is a U.S. National Phase patent application of International Patent Application No. PCT/US05/44935, filed Dec. 13, 2005, which claims the benefit of U.S. Provisional Patent Application No. 60/635,744, filed Dec. 13, 2004.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 6,091 Byte ASCII (Text) file named "701652ST25.TXT," created on Jun. 11, 2007.

FIELD OF THE INVENTION

This invention pertains to thermolabile prodrugs of oligonucleotides that contain a CpG motif, compositions thereof, and methods of inducing an immune response therewith.

BACKGROUND OF THE INVENTION

DNA is a complex macromolecule whose immunological activities are influenced by its base composition and base modification, as well as helical orientation. Certain unusual DNA structures (e.g., Z-DNA) can induce significant antibody responses when administered to normal mice. In addition, bacterial DNA, as well as certain synthetic oligodeoxynucleotides (ODN) containing unmethylated cytosine-guanine (CpG) sequences can induce cell proliferation and immunoglobulin (Ig) production in murine B cells.

Unmethylated CpG dinucleotides are more frequent in the genomes of bacteria and viruses than in vertebrates. Recent studies suggest that immune recognition of these motifs may contribute to the host's innate immune response. See, e.g., D. M. Klinman et al., *CpG Motifs Present in Bacterial DNA Rapidly Induce Lymphocytes to Secrete Interleukin 6, Interleukin 12, and Interferon γ*, 93 Proc. Natl. Acad. Sci. USA 2879 (1996); A.-K. Yi et al., *Rapid Immune Activation by CpG Motifs in Bacterial DNA*, 157 J. Immun. 5394 (1996); Hua Liang et al., *Activation of Human B Cells by Phosphorothioate Oligodeoxynucleotides*, 98 J. Clin. Invest. 1119 (1996); and A. M. Krieg et al., *CpG Motifs in Bacterial DNA Trigger Direct B-Cell Activation*, 374 Nature 546 (1995).

In mice, CpG oligonucleotides induces proliferation in almost all (>95%) B cells and increases Ig secretion. This B-cell activation by CpG DNA is T-cell independent and antigen non-specific. In addition to its direct effects on B cells, CpG DNA also directly activates monocytes, macrophages, and dendritic cells to secrete a variety of cytokines. These cytokines stimulate natural killer (NK) cells to secrete γ-inteferon (IFN-γ) and have increased lytic activity. See, e.g., WO 95/26204, WO 96/02555, WO 98/11211, WO 98/18810, WO 98/37919, WO 98/40100, WO 98/52581 and U.S. Pat. No. 5,663,153.

The development of immunostimulatory CpG oligonucleotides and therapeutic and prophylactic methods of using them is ongoing. For example, U.S. Pat. No. 6,194,388 describes the administration of CpG oligonucleotides ex vivo, e.g., by obtaining lymphocytes from a subject and stimulating the subject's lymphocytes ex vivo upon contact with an appropriate oligonucleotide, and in vivo, e.g., by administering a non-methylated CpG containing oligonucleotide to a subject to facilitate in vivo activation of a subject's lymphocytes. According to U.S. Pat. No. 6,194,388, activated lymphocytes, stimulated by ex vivo or in vivo, can boost a subject's immune response. Hence, the immunostimulatory oligonucleotides can be used to treat, prevent or ameliorate an immune system deficiency (e.g., a tumor or cancer or a viral, fungal, bacterial or parasitic infection) in a subject. In addition, immunostimulatory oligonucleotides can also be administered as a vaccine adjuvant, to stimulate a subject's response to a vaccine.

U.S. Pat. No. 6,194,388 also suggests that immunostimulatory CpG oligonucleotides may be useful for treating leukemia by increasing the sensitivity of chronic leukemia cells toward conventional ablative chemotherapy. U.S. Pat. No. 6,194,388 also describes neutral oligonucleotides (i.e. oligonucleotide that do not contain an umethylated CpG or which contain a methylated CpG dinucleotide), which can compete for binding with unmethylated CpG containing oligonucleotides. According to U.S. Pat. No. 6,194,388, the in vivo administration of neutral oligonucleotides should prove useful for treating diseases such as systemic lupus erythematosus, sepsis and autoimmune diseases, which are caused or exacerbated by the presence of umethylated CpG dimers in a subject. Immunostimulatory CpG oligonucleotides and therapeutic uses thereof also are described in U.S. Patent Application Publication Nos. US 2003/0060440; US 2003/0144229; US 2004/0105872; US 2004/0241841; US 2004/02488334 and U.S. Pat. Nos. 6,207,646; 6,239,116; 6,339,068; 6,406,705; 6,653,292 and 6,727,230.

Positive results of human clinical and preclinical trials have been reported. Coley Pharmaceutical Group reported positive results in human clinical trials investigating the effectiveness of an immunostimulatory CpG oligonucleotide (CpG 7909) against various cancers, and also reported positive preclinical results of the effectiveness of CpG 7909 against bioterror agents such as anthrax in rodents and monkeys.

However, the cellular delivery of CpG oligonucleotides is generally inefficient, particularly for highly negatively charged CpG ODNs. Further, certain types of CpG oligonucleotides have a strong tendency to form tetrads, making large-scale commercial production impractical. Moreover, CpG oligonucleotides can be highly susceptible to nuclease cleavage, rendering them inactive, and CpG oligonucleotides have a limited duration of action.

In view of the foregoing, there exists a need for CpG oligonucleotides with improved cellular delivery and nuclease resistance profile. In addition there is a need for CpG oligonucleotides for which the duration and/or onset of action can be controlled. There is also a need for therapeutically effective CpG oligonucleotides, which avoids tetrad formation, e.g., during manufacture and/or storage. The present invention provides such CpG oligonucleotides, formulations thereof and therapeutic methods of using them. These and other advantages of the invention, as well as additional inventive features, will be apparent from the description of the invention provided herein.

BRIEF SUMMARY OF THE INVENTION

The present invention provides oligonucleotides, which include a CpG motif ("CpG oligonucleotides"), functionalized with one or more thermolabile substituents. The thermolabile substituent is typically bonded to the non-bridging oxygen atom of at least one phosphate or phosphorothioate in the oligonucleotide. The present invention also provides compositions, which include a therapeutically effective amount of at least one thermolabile CpG oligonucleotide prodrug and a pharmacologically acceptable carrier. The present invention further provides methods of therapeutically administering the thermolabile CpG oligonucleotide prodrugs of the present invention, e.g., to induce an immune response.

The thermolabile CpG oligonucleotide prodrugs of the present invention can be administered to a host (e.g., a mammal) as a prodrug of the parent CpG oligonucleotides in vivo. The thermolabile CpG oligonucleotide prodrugs of the present invention are rapidly internalized by immune cells (B cells, macrophages, dendritic cells, and monocytes) and localized in endocytic vesicles where they can interact with Toll-like receptor 9. This interaction triggers an immunostimulatory cascade that is characterized by B-cell proliferation, dendritic cell maturation, natural killer cell activation and/or the secretion of a variety of cytokines, chemokines and polyreactive immunoglobulins. Administration of the thermolabile CpG oligonucleotide prodrugs of the present invention to a host, for example, can improve the resistance of the host against infectious pathogenic microorganisms, e.g., parasites, bacteria, and viruses.

BRIEF DESCRIPTION OF THE DRAWINGS

FIG. 8 depicts the sequence for comparative CpG ODN 1555 (SEQ ID: 1).

FIG. 9 depicts the sequence for CpG fma ODN 1555 (SEQ ID: 2), an exemplary CpG oligonucleotide prodrug of the present invention, where PS(fma) stands for a thermolytic 2-(N-formyl-N methyl)aminoethyl thiophosphate protecting group).

DETAILED DESCRIPTION

The present invention provides an oligonucleotide comprising at least one CpG motif (CpG oligonucleotide), wherein the oligonucleotide includes at least one thermolabile substituent, which is preferably bonded to the non-bridging oxygen atom of a phosphate or phosphorothioate in the oligonucleotide. In accordance with the present invention, suitable thermolabile substituents can include thermolabile phosphate, phosphorothioate and phosphoroselenoate protecting groups, which are useful in oligonucleotides synthesis, e.g., as described in U.S. Pat. No. 6,762,298 (Beaucage et al.).

In a preferred embodiment, the CpG oligonucleotide prodrug of the present invention is functionalized with at least one thermolabile substituent of the formula:

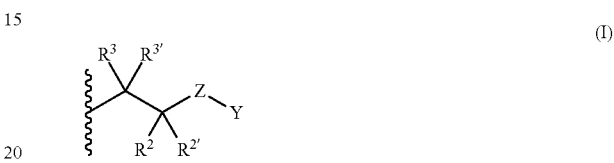

wherein:
$R^2$, $R^{2'}$, $R^3$ and $R^{3'}$ are the same or different and each is H, an alkyl, an alkenyl, an alkynyl, a cycloalkyl, an aryl, or an aralkyl, or $R^2$ or $R^{2'}$, in combination with $R^3$ or $R^{3'}$, together with the carbon atoms to which they are bonded, comprise a cyclic substituent of the formula:

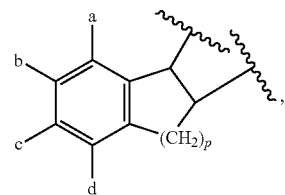

wherein p is an integer from 0-6 and a-d are the same or different and each is selected from the group consisting of H, an alkyl, a nitro, a dialkylamino, an alkoxy, an alkylthio, a cyano and a halogen;
Z is O, S, $NR^{4a}$, $CR^{4a}R^{4a'}$ or $CR^{4a}R^{4a'}CR^{4b}R^{4b'}$, wherein $R^{4a}$, $R^{4a'}$, $R^{4b}$ and $R^{4b'}$ are the same or different and each is H, an alkyl, an alkenyl, an alkynyl, a cycloalkyl, an aryl, or an aralkyl; and
Y is $CH_2R^1$, $C(X)R^1$ or a heterocyclic substituent comprising from 3 to about 10 atoms in the ring skeleton thereof, wherein X is O or S, and $R^1$ is H, $R^{1a}$, $OR^{1a}$, $SR^{1a}$ or $NR^{1a}R^{1a'}$, wherein $R^{1a}$ and $R^{1a'}$ are the same or different and each is H, an alkyl, an alkenyl, an alkynyl, a cycloalkyl, an aryl, or an aralkyl; or, when $R^1$ is $NR^{1a}R^{1a'}$, then $R^{1a}$ and $R^{1a'}$, together with the nitrogen atom to which they are bonded, or $R^{1a}$ or $R^{1a'}$, together with any of $R^{4a}$, $R^{4a'}$, $R^{4b}$ or $R^{4b'}$, form a ring containing from 3 to about 7 atoms in the ring skeleton thereof, wherein the substituent of formula (I) is thermolytically cleavable. Preferably, Y is not $CH_2R^1$ when Z is $CR^{4a}R^{4a'}CR^{4b}R^{4b'}$, and $R^1$ preferably is not H when Y is $CH_2R^1$ and Z is $CR^{4a}R^{4a'}$.

In accordance with the present invention, $R^{1a}$, $R^{1a'}$, $R^2$, $R^{2'}$, $R^3$, $R^{3'}$, $R^{4a}$, $R^{4a'}$, $R^{4b}$ and $R^{4b'}$ can be unsubstituted or substituted with one or more substituents, which are the same or different, selected from the group consisting of $OR^5$, $SR^5$, CN, $NO_2$, $N_3$, and a halogen, wherein $R^5$ is H or an alkyl.

Figure 3:
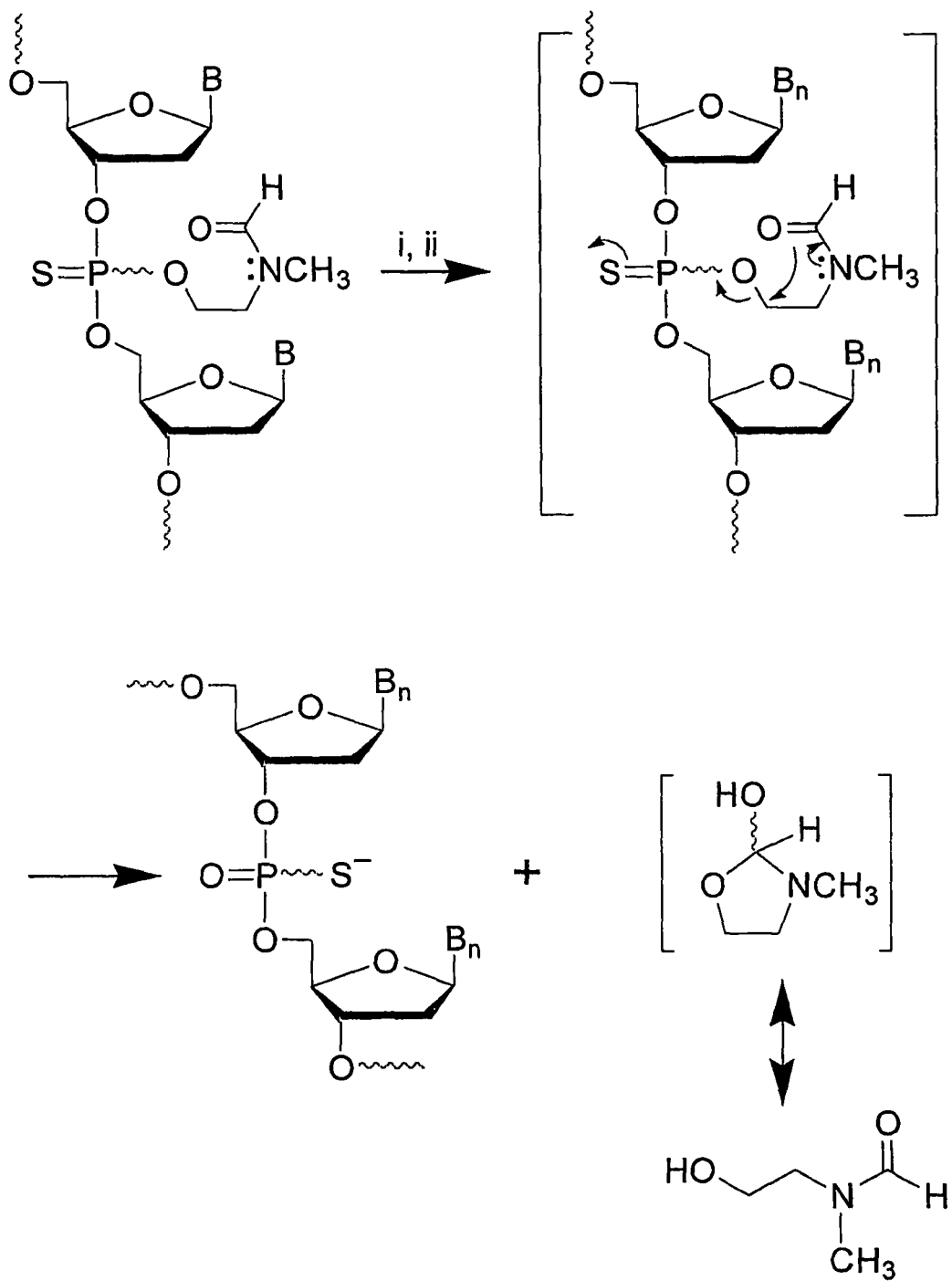
FIG. 3 illustrates one possible in vivo mechanism of the thermolytic conversion of an exemplary CpG oligonucleotide prodrug of the present invention.

Although not wishing to be bound by any particular theory, it is believed that the bond linking the substituent of formula (I) to the phosphorus group, e.g., through a non-bridging oxygen atom of the phosphate or phosphorothioate is cleaved thermally in vivo. The resulting thermolytic cleavage releases (or activates) the parent CpG oligonucleotide, which, in turn, provides the desired therapeutic effect. One possible mechanism for the in vivo thermolytic cleavage is illustrated in FIG. 3.

The CpG oligonucleotide prodrug of the present invention includes a thermolabile substituent, e.g., of formula (I), which is chemically bonded to at least one nucleotide, e.g., covalently bonded to the non-bridging oxygen atom of at least one phosphate or phosphorothioate in the oligonucleotide. The thermolabile substituent can be bonded to a nucleotide within the CpG motif sequence. If the CpG oligonucleotide comprises a poly-G tail, then the thermolabile substituent can be bonded to the non-bridging oxygen atom of the phosphate or phosphorothioate of at least one nucleotide in the poly-G tail.

By using different structural combinations, e.g., of $R^1$, $R^{1a}$, $R^{1a'}$, $R^2$, $R^{2'}$, $R^3$, $R^{3'}$, $R^{4a}$, $R^{4a'}$, $R^{4b}$ and $R^{4b'}$, $R^5$, Z, Y and/or X of formula (I), the structure of the thermolabile group can be modified to adjust the thermolability to a desired level to optimize the therapeutic efficacy for a particular application. It is believed that the therapeutic effect of the CpG oligonucleotide can be delayed (e.g., to delay the onset of action) or sustained (e.g., to prolong the duration of action) by structurally modifying the thermolabile substituent, e.g., of formula (I), to optimize the thermolability for a specific therapeutic application in accordance with the present invention. It is also believed that the onset and/or duration of therapeutic efficacy can be controlled by administering multiple CpG oligonucleotide prodrugs of the present invention, which vary structurally in terms of the thermolabile substituent(s) to release (activate) the parent CpG oligonucleotide at different rates.

In addition, the structure and the number of thermolabile substituents on the CpG oligonucleotide can be varied to impart desirable physicochemical and/or pharmacological properties. For instance, the polarity of the thermolabile substituent can be varied to promote desirable physicochemical properties, e.g., solubility and stability, of the CpG oligonucleotide prodrug. In addition, the polarity of the thermolabile substituent can be varied to promote desirable pharmacological properties, e.g., enhanced cellular delivery, increased resistance against nuclease degradation, improved bioavailability, and the like. Alternatively (or additionally), the number of thermolabile substituents can be decreased or increased to control the number of free phosphates and/or phosphorothioates, which can also promote desirable solubility properties of the CpG oligonucleotide prodrug. The CpG oligonucleotide prodrugs of the present invention also do not have a tendency to form tetrads, thereby avoiding one of the greatest difficulties associated with commercial scale production of therapeutic compounds that include the CpG motif.

As utilized herein, the term "alkyl" means a straight-chain or branched-chain alkyl radical which, unless otherwise specified, contains from about 1 to about 20 carbon atoms, preferably from about 1 to about 10 carbon atoms, more preferably from about 1 to about 8 carbon atoms, and most preferably from about 1 to about 6 carbon atoms. Examples of such alkyl radicals include methyl, ethyl, propyl, isopropyl, n-butyl, sec-butyl, isobutyl, tert-butyl, pentyl, isoamyl, hexyl, octyl, dodecanyl, and the like.

The term "alkenyl" means a straight-chain or branched-chain alkenyl radical, which has one or more double bonds and, unless otherwise specified, contains from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

The term "alkynyl" means a straight-chain or branched-chain alkynyl radical, which has one or more triple bonds and contains from about 2 to about 20 carbon atoms, preferably from about 2 to about 10 carbon atoms, more preferably from about 2 to about 8 carbon atoms, and most preferably from about 2 to about 6 carbon atoms. Examples of alkynyl radicals include ethynyl, propynyl (propargyl), butynyl, and the like.

The terms "alkylamino" and "dialkylamino" mean an alkyl or a dialkyl amine radical, wherein the term "alkyl" is defined as above. Examples of alkylamino radicals include methylamino ($NHCH_3$), ethylamino ($NHCH_2CH_3$), n-propylamino, isopropylamino, n-butylamino, isobutylamino, sec-butylamino, tert-butylamino, n-hexylamino, and the like. Examples of dialkylamino radicals include dimethylamino ($N(CH_3)_2$), diethylamino ($N(CH_2CH_3)_2$), di-n-propylamino, diisopropylamino, di-n-butylamino, diisobutylamino, di-sec-butylamino, di-tert-butylamino, di-n-hexylamino, and the like.

The term "cycloalkyl" means a monocyclic alkyl radical, or a polycyclic alkyl which comprises one or more alkyl carbocyclic rings, which can be the same or different when the polycyclic radical has 3 to about 10 carbon atoms in the carbocyclic skeleton of each ring. Preferably, the cycloalkyl has from about 4 to about 7 carbon atoms, more preferably from about 5 to about 6 carbons atoms. Examples of monocyclic cycloalkyl radicals include cyclopropyl, cyclobutyl, cyclopentyl, cyclohexyl, cycloheptyl, cyclodecyl, and the like. Examples of polycyclic cycloalkyl radicals include decahydronaphthyl, bicyclo[5.4.0]undecyl, adamantyl, and the like.

The term "aryl" refers to an aromatic carbocyclic radical, as commonly understood in the art, and includes monocyclic and polycyclic aromatics such as, for example, phenyl and naphthyl radicals, which radicals are, unless indicated otherwise, unsubstituted or substituted with one or more substituents selected from the group consisting of a halogen, an alkyl, an alkoxy, an amino, a cyano, a nitro, and the like. Preferably, the aryl has one or more six-membered cyclic rings including, for example, phenyl, naphthyl, biphenyl, and are unsubstituted or substituted as set forth herein.

The term "aralkyl" means alkyl as defined herein, wherein an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like.

The terms heterocycle and heterocyclic refer to both heterocycloalkyls and heteroaryls. Heterocycloalkyls include cycloalkyls (including polycyclics), wherein at least one carbon of a carbocyclic ring is substituted with a heteroatom such as, for example, O, N, or S. The heterocycloalkyl optionally has one or more double bonds within a ring, and may be aromatic, but it is not necessarily aromatic. The heterocycloalkyl preferably has 3 to about 10 atoms (members) in the skeleton of each ring, more preferably from about 3 to about 7 atoms, more preferably from about 5 to about 6 atoms. Examples of heterocycloalkyl radicals include epoxy, aziridyl, oxetanyl, tetrahydrofuranyl, dihydrofuranyl, piperidinyl, piperazinyl, pyranyl, morpholinyl, and the like. Heteroaryls include aromatic heterocyclic rings in accordance with what is commonly understood in the art, including monocyclic radicals such as, for example, imidazole, thiazole, pyrazole, pyrrole, furane, pyrazoline, thiophene, oxazole, isoxazole, pyridine (e.g., 2-pyridyl), pyridone, pyrimidine, cytosine, 5-methylcytosine, thymine, pyrazine, triazine radicals, and polycyclics such as, for example, quinoline, isoquinoline, indole, purine, adenine, guanine, N6-methyladenine, and benzothiazole radicals, which heteroaryl radicals are unsubstituted or substituted with one or more substituents, which are the same or different, selected from the group consisting of a halogen, an alkyl, an alkoxy, an amino, a cyano, a nitro, and the like. The heteroaryl preferably has 3 to 7 atoms, more preferably from 5 to 6 atoms, in the ring skeleton thereof.

It will be appreciated that the heterocyclic substituents can be coupled to the compounds of the present invention via a heteroatom, such as nitrogen (e.g., 1-imidazolyl), or via a carbon atom (e.g., 4-thiazolyl). It will also be appreciated that heteroaryls, as defined herein, are not necessarily "aromatic" in the same context as phenyl is aromatic, although heteroaryls nonetheless demonstrate physical and chemical properties associated with aromaticity, as the term is understood in the art.

The term "carboxyl" means any functional group with a carbonyl backbone, and includes functional groups such as, for example, a carboxylic acid, an ester (e.g., ethoxycarbonyl), and amides (e.g., benzamido).

In one embodiment, the non-bridging oxygen atom of at least one phosphate or phosphorothioate of the CpG oligonucleotide is functionalized with a thermolabile substituent of formula (I), wherein $R^2$, $R^{2'}$, $R^3$ and $R^{3'}$ are all hydrogen. In another embodiment, the non-bridging oxygen atom of at least one phosphate or phosphorothioate in the CpG oligonucleotide is functionalized with a thermolabile substituent of formula (I), wherein Z is $CR^{4a}R^{4a'}$ or $CR^{4a}R^{4a'}CR^{4b}R^{4b'}$ and $R^{4a}$, $R^{4a'}$, $R^{4b}$ and $R^{4b'}$ are all hydrogen, or wherein Z is $NR^{4a}$ and $R^{4a}$ is alkyl (e.g., methyl). Examples of Z include, e.g., $CH_2$ (methylene), $CH_2CH_2$ (ethylene), $N(CH_3)$ (methylamino), and the like. In another embodiment, the non-bridging oxygen atom of at least one phosphate or phosphorothioate in the CpG oligonucleotide is functionalized with a thermolabile substituent of formula (I), wherein Y is $CH_2R^1$ or $C(O)R^1$ and $R^1$ is H, OH, $R^{1a}$, $SR^{1a}$ or $NR^{1a}R^{1a'}$, wherein $R^{1a}$ is alkyl (e.g., methyl or tert-butyl) and $R^{1a'}$ is H. Examples of Y include, e.g., $CH_2OH$ (hydroxymethyl), $CH_2SCH_3$ (methylthiomethyl), $C(O)H$ (formyl), $C(O)CH_3$ (methylcarbonyl), $C(O)NHC(CH_3)_3$ (tert-butylaminocarbonyl), and the like. In yet another embodiment, Y is a heterocycle, which is preferably pyridyl (e.g., 2-pyridyl). Examples of structural combinations Z and Y together (i.e., "Z-Y" combinations of formula (I)) include, e.g., $N(CH_3)C(O)H$; $CH_2C(O)CH_3$, $CH_2C(O)NHC(CH_3)_3$; 2-pyridylmethyl; $N(CH_3)(2$-pyridyl); $CH_2CH_2SCH_3$ and $CH_2CH_2OH$.

Exemplary thermolabile substituents of formula (I) include the following:

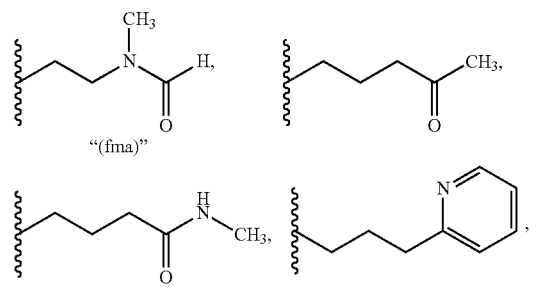

"(fma)"

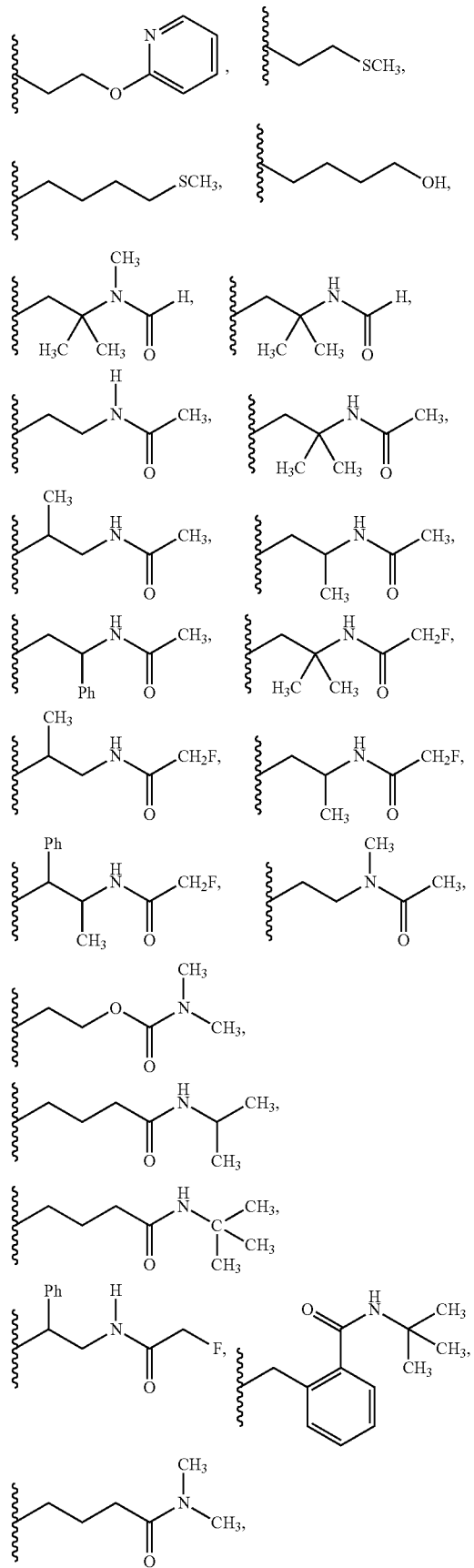

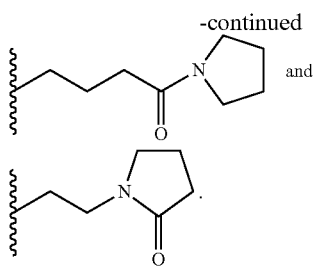

Preferred thermolabile substituents of formula (I) include the following:

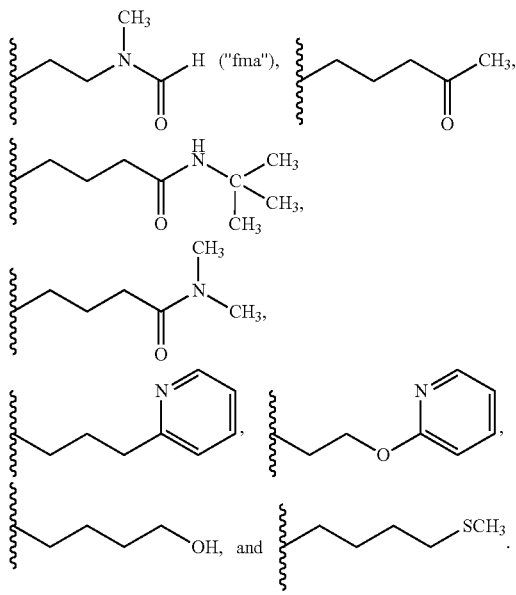

The thermolabile protecting group is removed thermolytically from the CpG oligonucleotide prodrugs the present invention preferably at a substantially neutral pH, e.g., from about 5.5-7.5, preferably from about 6-7.5, most preferably about 7 (e.g., about 7.0-7.4). The thermolabile substituent of CpG oligonucleotide prodrug of the present invention is preferably thermolabile at a temperature that correlates to the body temperature of a mammal, e.g., a human.

The present invention can be used in the delivery of any suitable CpG oligonucleotide, including the immunostimulatory CpG oligonucleotides described in U.S. Patent Application Publication Nos. US 2003/0060440; US 2003/0144229; US 2004/0105872; US 2004/0241841 and US 2004/02488334, and U.S. Pat. Nos. 6,194,388, 6,207,646; 6,239,116; 6,339,068; 6,406,705; 6,653,292 and 6,727,230. The structures of the CpG oligonucleotide prodrugs of the present invention can include modified and/or naturally occurring nucleosides, including furanosides found in nucleic acids and derivatives thereof. Naturally occurring nucleosides include, for example, adenosine, guanosine, cytidine, thymidine, and uridine. Nucleoside derivatives also include nucleosides having modified base moieties, with or without protecting groups. Such analogs include, for example, deoxyinosine, 2,6-diaminopurine-2'-deoxyriboside, 5-methyl-2'-deoxycytidine, and the like. The base rings most commonly found in naturally occurring nucleosides are purine and pyrimidine rings. Naturally occurring purine rings include, for example, adenine, guanine, and $N^6$-methyladenine. Naturally occurring purine rings include, for example, cytosine, thymine, and 5-methylcytosine. Moreover, nucleoside derivatives include other purine and pyrimidine derivatives, for example, halogen-substituted purines (e.g., 6-fluoropurine), halogen-substituted pyrimidines, $N^6$-ethyladenine, $N^6$-(alkyl)-cytosines, 5-ethylcytosine, and the like.

The CpG oligonucleotide prodrugs of the present invention can include any suitable number of nucleotides (e.g., 2 nucleotides, from 2 to 6 nucleotides, from 2 to about 10 nucleotides, from 2 to about 20 nucleotides, from 2 to about 40 nucleotides, from 2 to about 60 nucleotides, or from 2 to about 100 nucleotides (e.g., from 6 to about 100 nucleotides, from 6 to about 80 nucleotides, from 6 to about 50 nucleotides, from 6 to about 40 nucleotides, from 6 to about 30 nucleotides, or from 6 to about 20 nucleotides).

As indicated above, the thermolabile CpG oligonucleotide prodrugs of the present invention include oligonucleotides with at least one CpG motif, e.g., A-type, B-type, C-type, D-type, or K-type CpG oligonucleotides. Specific, non-limiting examples of D-type and K-type CpG oligonucleotides can be found, e.g., in Verthelyi et al., *J. Immunol.,* 166, pp. 2372-2377 (2001). Specific, non-limiting, examples of C-type oligonucleotides can be found, e.g., in Hartmann et al., *Eur. J. Immunol.,* 33, pp. 1633-1641 (2003).

In one embodiment, the CpG oligonucleotide prodrug of the present invention includes a thermolabile functionalized K-type oligodeoxynucleotide ("ODN"). K-type ODNs, which are known to exhibit potent immunostimulatory activity, share specific characteristics, which differ from those of the D-type ODNs. In addition, K-type ODNs reportedly have specific effects on the cells of the immune system, which differ from the effects of D-type ODNs. For example, K-type ODNs have been shown to stimulate the proliferation of B cells and the production of IL-6. The K-type ODNs typically are at least about 10 nucleotides in length and can include the following sequence:

5' $N_1N_2N_3$T-CpG-W$N_4N_5N_6$ 3', wherein the central CpG motif is umethylated, W is A or T, and $N_1$, $N_2$, $N_3$, $N_4$, $N_5$, and $N_6$, are any nucleotide.

In another embodiment, the CpG oligonucleotide prodrug of the present invention includes a thermolabile functionalized K-type ODN that induces a humoral immune response. K-type ODNs have been shown to stimulate B cell proliferation and the secretion of IgM and IL-6, processes involved in the body's humoral immunity, such as the production of antibodies against foreign antigens. K-type ODNs containing CpG motifs at the 5' end are preferred, although at least one base upstream of the CpG is desirable. Also preferred are the K-type ODNs that contain a thymidine immediately 5' from the CpG dinucleotide, and a TpT or a TpA in a position 3' from the CpG motif. Modifications which are greater than 2 base pairs from the CpG dinucleotide motif do not appear to significantly impact K type ODN activity.

K-type CpG ODNs can include modified nucleotides. Any suitable modification can be used to render the ODNs resistant to in vivo degradation resulting from, e.g., exo or endonuclease digestion. In one embodiment, the modification includes a phosphorothioate modification. The phosphorothioate modifications can occur at either termini, e.g., the last two or three 5' and/or 3' nucleotides can be linked with phosphorothioate bonds. The ODNs also can be modified to contain a secondary structure (e.g., stem loop structure) such that it is resistant to degradation. Another modification that renders the ODN less susceptible to degradation is the inclusion of nontraditional bases such as, e.g., inosine, as well as acetyl-, thio-, and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

In another embodiment, the CpG oligonucleotide prodrug of the present invention includes a thermolabile functionalized D-type ODN. D-type ODNs differ both in structure and activity from K-type ODNs. For example, as disclosed herein, D-type ODNs stimulate the release of cytokines from cells of the immune system. For example, D-type ODNs can stimulate the release or production of IP-10 and IFN-α by monocytes and/or plasmacitoid dendritic cells and the release or production of IFN-γ by NK cells. The stimulation of NK cells by D type ODNs can be either direct or indirect.

An exemplary CpG motif in a D-type oligonucleotide is as follows:

5' RY-CpG-RY 3', wherein the central CpG motif is unmethylated, R is A or G (a purine), and Y is C or T (a pyrimidine). D-type ODNs typically include an unmethylated CpG dinucleotide. Inversion, replacement, or methylation of the CpG has been shown to reduce or abrogate the activity of the D-type ODNs.

D-type CpG ODNs can include modified nucleotides, e.g., to increase the stability of the D-type CpG ODN. While not wishing to be bound by any particular theory, it is believed that because phosphorothioate-modified nucleotides confer resistance to exonuclease digestion, the D-type CpG ODNs are "stabilized" by incorporating phosphorothioate-modified nucleotides. In one embodiment, the CpG dinucleotide motif and its immediate flanking regions include phosphodiester rather than phosphorothioate nucleotides. In accordance with the present invention, any suitable modification can be made, e.g., to render the ODNs more resistant to degradation in vivo (e.g., via an exo- or endo-nuclease). For instance, the inclusion of nontraditional bases such as inosine as well as acetyl-, thio-, and similarly modified forms of adenine, cytidine, guanine, thymine, and uridine, may render the ODN less susceptible to degradation.

Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters, and alkylphosphotriesters (i.e., the charged oxygen moiety is alkylated, as described in U.S. Pat. No. 5,023,243 and European Patent No. 0 092 574). ODNs containing a diol, such as tetraethyleneglycol or hexaethyleneglycol, at either or both termini, have also been shown to be more resistant to degradation. The D-type ODNs can also be modified to contain a secondary structure (e.g., stem loop structure). While not wishing to be bound by any particular theory, it is believed that incorporation of a stem loop structure can improve the efficacy of the ODN. Specific, non-limiting examples of D-type ODNs can be found in U.S. Patent Application Publication No. US 2003/0060440.

In yet another embodiment, the CpG oligonucleotide prodrug of the present invention includes a thermolabile functionlized ODN with a poly-G tail. A poly-G tail comprises at least two guanine (G) nucleotides at the end of the molecule, e.g., as shown in the following sequence:

5' GGX$_1$X$_2$X$_3$ Pu$_1$ Py$_2$ CpG Pu$_3$ Py$_4$ X$_4$X$_5$X$_6$(W)$_M$ (G)$_N$- 3'.

In a preferred embodiment, the present invention provides synthetic single-stranded DNA oligonucleotide phosphorothioates containing unmethylated CpG motifs, wherein the oligonucleotide contains and at least one thermolabile substituent, e.g., of formula (I). The CpG motif sequence can include, e.g., a human CpG motif sequence, a mouse CpG motif sequence, or a homolog thereof. SEQ ID NO: 2 (FIG. 9) is an exemplary thermolabile CpG oligonucleotide prodrug of the present invention.

The present invention further provides a pharmaceutical composition which includes a carrier and a therapeutically effective amount of at least one CpG oligonucleotide prodrug of the present invention. The composition can be formulated based upon factors such as, e.g., the route of administration, whether the composition will be used in vivo or an ex vivo, and the like. One of skill in the art can readily select a suitable route of administration, including, but not limited to intravenous, intramuscular, intraperitoneal, transmucosal, subcutaneous, transdermal, intranasal, and oral administration.

The pharmaceutical composition of the present invention may be in a form suitable for oral use such as, for example, tablets, troches, lozenges, aqueous or oily suspensions, dispersible powders or granules, emulsions, hard or soft capsules, syrups or elixirs. Compositions intended for oral use may be prepared according to any method known in the art for the manufacture of pharmaceutical compositions, and such compositions can contain one or more agents including, for example, sweetening agents, flavoring agents, coloring agents, and preserving agents in order to provide a pharmaceutically elegant and/or palatable preparation.

Tablets can contain the active ingredient in admixture with non-toxic pharmaceutically acceptable excipients which are suitable for manufacture of tablets. Such excipients can include, for example, inert diluents such as, for example, calcium carbonate, lactose, calcium phosphate or sodium phosphate; granulating and disintegrating agents such as, for example, maize starch or alginic acid; binding agents such as, for example, starch, gelatine or acacia, and lubricating agents such as, for example, stearic acid or talc. The tablets may be uncoated, or they may be coated by known techniques to delay disintegration and absorption in the gastrointestinal tract and thereby provide a sustained action over a longer period. A time delay material, for example, glyceryl monostearate or glyceryl distearate, alone or with a wax, may be employed. Formulations for oral use also can be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions typically contain the active materials in admixture with excipients suitable for the manufacture of aqueous suspensions. Such excipients include suspending agents, for example, sodium carboxymethyl cellulose, methylcellulose, hydroxypropylmethylcellulose, sodium alginate, polyvinylpyrrolidone, gum tragacanth and gam acacia. Dispersing or wetting agents may include natural-occurring phosphatides, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example, polyoxyethylene sorbitan monooleate. The aqueous suspensions also can contain one or more preservatives, for example, ethyl or n-propyl p-hydroxy benzoate, one or more coloring agents, one or more flavoring agents and one or more sweetening agents such as, for example, sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions can be preserved by the addition of an antioxidant such as, for example, ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, also may be present.

The composition of the present invention also can be in the form of oil-in-water emulsions. The oily phase can be a vegetable oil, for example, olive oil or arachis oils, or a mineral oil, for example liquid paraffin or mixtures of these. Suitable emulsifying agents may be naturally-occurring gums, for example gum acacia or gum tragacantn, naturally-occurring phosphatides, for example soya bean lecithin, and esters or partial esters derived from fatty acids and hexitol anhydrides, for example sorbitan mono-oleate, and condensation products of the said partial esters and ethylene oxide, for example polyoxyethylene sorbitan mono-oleate. The emulsions also can contain sweetening and flavoring agents.

The composition of the present invention can be in the form of syrups and elixirs, which are typically formulated with sweetening agents such as, for example, glycerol, sorbitol or sucrose. Such formulations also can contain one or more demulcents, preservatives, flavoring agents and coloring agents.

The pharmaceutical composition of the present invention also can be in the form of a sterile injectable preparation, for example, as a sterile injectable aqueous or oleagenous suspension. Suitable suspensions for parenteral administration can be formulated according to the known art using those suitable dispersing or wetting agents and suspending agents which have been mentioned above. Formulations suitable for parenteral administration also can include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The sterile injectable preparation can be in the form of a solution or a suspension in a non-toxic parenterally-acceptable diluent or solvent, for example, as a solution in water or 1,3-butanediol. Among the acceptable vehicles and solvents that can be employed, for example, are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as, for example, oleic acid find use in the preparation of injectables.

The CpG oligonucleotide prodrugs of the present invention also can be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols. Formulations suitable for vaginal administration can be presented as pessaries, tampons, creams, gels, pastes, and foams.

Formulations suitable for topical administration may be presented as creams, gels, pastes, or foams, containing, in addition to the active ingredient, such carriers as are known in the art to be appropriate.

The CpG oligonucleotide prodrugs of the present invention, alone or in combination with other suitable components, can be made into aerosol formulations to be administered via inhalation. These aerosol formulations can be placed into pressurized acceptable propellants, such as dichlorodifluoromethane, fluorocarbons (e.g., HFA 134a, HFA 227), propane, nitrogen, and the like. They also can be formulated as pharmaceuticals for non-pressured preparations such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Any suitable dosage level can be employed in the pharmaceutical compositions of the present invention. The dose administered to an animal, particularly a human, in accordance with the present invention should be sufficient to effect a prophylactic or therapeutic response in the animal over a reasonable time frame. The amount of active ingredient that can be combined with the carrier materials to produce a single dosage form will vary depending upon the host treated and the particular mode of administration. One skilled in the art will recognize that the specific dosage level for any particular patient will depend upon a variety of factors including, for example, the activity of the specific compound employed, the age, body weight; general health, sex, diet, time of administration, route of administration, rate of excretion, and the severity of the particular disease undergoing therapy. The size of the dose will also be determined by the existence, nature, and extent of any adverse side-effects that might accompany the administration of a particular compound. Other factors which effect the specific dosage include, for example, bioavailability, metabolic profile, and the pharmacodynamics associated with the particular compound to be administered in a particular patient.

Suitable doses and dosage regimens can be determined by comparisons, for example, with the parent CpG oligonucleotides or with other CpG oligonucleotides that are known to promote comparable therapeutic (e.g., anti-infective) responses. Suitable doses and dosage regimens also can be determined by comparisons with other types of agents that are known to exhibit comparable therapeutic efficacy. Preferred dosages can include amounts, which result, e.g., in the prevention or inhibition of an infection, or in the inhibition of cancer metastasis, without significant side effects. In proper doses and, optionally, in combination with the administration of certain compounds, the compositions of the present invention can be formulated to provide, e.g., partial to essentially complete inhibition of symptoms associated with infection by a disease-causing organism or, in the case of cancer, partial to essentially complete inhibition of metastasis.

The present invention further provides a method of inducing an immune response in a host (for example, a mammal such as, e.g., a human) comprising administering to the host at least one CpG oligonucleotide prodrug of the present invention in an amount effective to induce an immune response in the host. The immune response can include, e.g., an immunostimulatory response, an immunomodulatory response or an immunosuppressive response.

A CpG oligonucleotide prodrug can be administered in accordance with the method of the present invention in an amount effective to induce a cell-mediated or a humoral immune response in the host. In a preferred embodiment, the CpG oligonucleotide prodrugs administered in accordance with the present invention are K-type ODNs, and the immune response is a humoral immune response. Parameters of the humoral immune response include, but are not limited to, IgM production, IL-6 production, and/or proliferation. Thus, in one embodiment, the immune response comprises proliferation of peripheral blood mononuclear cells, IgM production, IL-6 production, or a combination thereof. In another embodiment, thermolabile functionalized D-type ODNs are used to produce an immune response in a subject. Administration of a D-type ODN activates monocytes and/or natural killer cells, and induces the maturation of dendritic cells. Furthermore, a D-type ODN can be used to increase the production of cytokines (for example IL-10, IFN-$\alpha$ or IFN-$\gamma$) by a cell of the immune system.

Alternatively, a CpG oligonucleotide prodrug can be administered in accordance with the method of the present invention to induce cytokine production in the host. The cytokine produced may include, for example, an interferon, e.g., interferon-$\alpha$ (interferon-alpha), interferon-$\beta$ (interferon-beta) or interferon-$\gamma$ (interferon-gamma). The method of the present invention also can be effective to activate B cells in the host, induce IL-6 production in the host, induce antibody production in the host, induce IFN-$\alpha$ production in the host, or induce dendritic cell activation and/or dendritic cell maturation in the host.

Additionally, a CpG oligonucleotide prodrug can be administered in accordance with the present invention to treat, prevent, or ameliorate an allergic reaction in a subject (e.g., when used in combination with a known antiallergenic agent). Allergies can include acquired hypersensitivities to an allergenic substance (i.e., an allergen). Allergic conditions include eczema, allergic rhinitis or coryza, hay fever, asthma, uticaria (hives), food allergies, and other atopic conditions. Allergens can include, e.g., pollens, insect venoms, animal dander, dust, fungal spores, and drugs (e.g., penicillin). Examples of natural, animal, and plant allergens can be found in International Patent Application WO 98/18810. In one embodiment, a thermolabile CpG oligonucleotide prodrug is administered to a subject to treat allergic asthma. The thermolabile CpG oligonucleotide prodrugs of the present invention also can be administered in combination with any suitable anti-allergenic agent. Suitable anti-allergenic agents include those substances given in treatment of the various allergic conditions described above, examples of which can be found in the Physicians' Desk Reference, 56$^{th}$ Ed. (2002).

One or more thermolabile CpG oligonucleotide prodrugs of the present invention can be effective for treating or preventing a neoplasm. The thermolabile CpG oligonucleotide prodrugs can be administered alone or in combination with any suitable anti-neoplastic agent, such as a chemotherapeutic agent or radiation. Suitable neoplasms include, but are not limited to, solid tumors such as cancers of the brain, lung (e.g., small cell and non-small cell), ovary, breast, bladder (e.g., transitional bladder cancer), prostate, and colon, as well as carcinomas and sarcomas.

One or more thermolabile CpG oligonucleotide prodrugs can be administered in accordance with the method of the present invention to increase the therapeutic efficacy of a vaccine. Suitable vaccines include those directed against Leishmania, Hepatitis A, B, and C, examples of which can be found in the Physicians' Desk Reference (1998), and DNA vaccines directed against, for example, HIV and malaria. (See generally, Klinman et al., 17 Vaccine 17: 19, 1999; McCluskie and Davis, J. Immun. 161:4463, 1998).

The method of the present invention also can be applied toward treating, preventing, or ameliorating a disease associated with the immune system. Such diseases can include, e.g., autoimmune disorders and immune system deficiencies. Examples of autoimmune diseases include, but are not limited to diabetes, rheumatoid arthritis, lupus erythematosus, and multiple sclerosis. Immune system deficiencies include those diseases or disorders in which the immune system is not functioning at normal capacity, or in which it would be useful to boost the immune system response.

The thermolabile CpG oligonucleotide prodrugs also can be used for treating or preventing infection by pathogenic microorganisms, such as bacteria, viruses and parasites. The thermolabile CpG oligonucleotide prodrugs of the present invention can be administered to a subject infected with or exposed to an infectious amount of the infectious agent. The thermolabile CpG oligonucleotide prodrugs of the present invention can be administered alone or in combination with any suitable anti-infectious agent, such as an antiviral, anti-fungal or anti-bacterial agent (see Physicians' Desk Reference, 1998). Specific, non-limiting examples of infectious agents include, e.g., tularemia, francisella, schistosomiasis, tuberculosis, malaria, and leishmaniasis. Others include, e.g., viruses, bacteria, fungi, parasites, and other organisms (e.g., protists) described in WO 98/18810.

The method of the present invention also can be effective for treating or preventing infection by a bio-warfare agent in humans (e.g., to protect soldiers who are at risk of being harmed from exposure to bio-warfare agents). Bio-warfare agents can include, e.g., naturally occurring biological agents and those, which have been specifically modified in the laboratory. Examples include Ebola, Anthrax, and Listeria. In the course of preventing or treating infection or symptoms associated with exposure to a bio-warfare agent, a thermolabile CpG oligonucleotide prodrugs can be administered in accordance with the present invention in an amount effect to cure the subject or extend the subject's life sufficiently to make it possible for the subject to seek more extensive treatment.

In accordance with the present invention, the thermolabile CpG oligonucleotide prodrugs can be modified to delay the onset of and/or prolong the immune response in the host. For example, the method of the present invention provides for inducement of an immune response in the host, e.g., about 12 hours or longer, about 24 hours or longer, about 36 hours or longer, about 48 hours or longer, about 72 hours or longer, or about 96 hours or longer after administration of the thermolabile CpG oligonucleotide prodrug.

The present invention also provides a method of inducing an immune response in a host by contacting cells with at least one thermolabile CpG oligonucleotide prodrug of the present invention ex vivo to produce activated immune cells, and administering the activated immune cells in an amount effective to induce an immune response in the host. The thermolabile CpG oligonucleotide prodrug may be administered to peripheral blood cells, monocytes, or lymphocytes ex vivo, thereby producing activated cells (e.g., activated dendritic cells and activated lymphocytes), followed by administration of a therapeutically effective amount of the activated cells to produce an immune response in the host.

In one embodiment, a method is provided for inducing an immune response in a subject wherein the method includes contacting a monocyte or a dendritic cell precursor in vitro with thermolabile functionalized D-type ODNs to produce an activated antigen presenting cell. The monocytes or dendritic cell precursors can be contacted with the thermolabile functionalized D-type ODNs in the presence of or in the absence of antigen. The activated antigen presenting cell is then administered to the subject to induce an immune response.

In another embodiment, a method is provided herein for inducing an immune response in a subject that includes contacting a monocyte or a dendritic cell precursor in vitro with a thermolabile functionalized D type-ODN to produce an activated antigen presenting cell. The monocytes or dendritic cell precursors can be contacted with the thermolabile functionalized D-type ODNs in the presence of or in the absence of antigen. Lymphocytes or natural killer cells are then contacted with the activated antigen presenting cells in vitro, or with cytokines secreted by the activated antigen presenting cells in vitro, to produce activated lymphocytes or activated natural killer cells. The activated lymphocytes or natural killer cells are then administered to the subject to induce the immune response.

The immune response may manifest itself immediately after the ODN is administered to the host. In an alternate embodiment, the immune response occurs after a period of time subsequent to the administration of ODN to the host. For example, the immune response is induced about 12 hours or more, about 18 hours or more, about 24 hours or more, about 30 hours or more, about 36 hours or more, about 48 hours or more, about 72 hours or more, or about 96 hours or more after administration of the ODN.

Thermolabile CpG oligonucleotide prodrugs of the present invention also can be used in combination with any suitable antisense therapy. Suitable antisense agents are those that bind either with DNA or RNA and block their function by inhibiting expression of the sequence to which the antisense agents are bound. See, e.g., Lonnberg et al., *Ann. Med.*, 28, 511-522 (1996); Alama et al., *Pharmacol. Res.*, 36, 171-178 (1997); and Scanlon et al., *FASEB J.*, 1288-1296 (1995).

The present invention further provides a method of inhibiting tetrad formation in a CpG oligonucleotide by functionalizing the CpG oligonucleotide with one or more thermolabile substituents to reduce the tendency of the parent CpG oligonucleotide to undergo tetrad formation. Such tetrads have a strong tendency to precipitate from solution under manufacturing and/or storage conditions. The method of inhibiting tetrad formation of the present invention can reduce or even eliminate the formation of tetrads during manufacturing and/or storage, yet allows the parent CpG oligonucleotide to function naturally (and form tetrads if necessary) in vivo upon removal of the one or more thermolabile substituents. Hence, the method of inhibiting tetrad formation of the present invention does not require alteration of the underlying structure of the parent CpG oligonucleotide.

The tetrad-forming tendency of the prodrug can be monitored, e.g., as a function of the number and/or position of the one or more thermolabile substituents using methods that are well known in the art (e.g., CD spectra). The number and position(s) of the thermolabile substituents can be tailored to the structure of a particular CpG oligonucleotide, taking into account factors such as, e.g., the inherent tetrad-forming tendency of the parent CpG oligonucleotide, the particular therapeutic application, the particular commercial application, how the product is formulated, the storage conditions, and the like.

The method of reducing tetrad formation of the present invention preferably includes functionalizing the CpG oligonucleotide with one or more thermolabile substituents of formula (I) as described herein. In one embodiment, the parent oligonucleotide is D-type or an A-type CpG oligodeoxynucleotide. In another embodiment, the parent oligonucleotide has a poly-G tail. Exemplary parent oligonucleotides, which can be functionalized to inhibit tetrad formation in accordance with the present invention, include, e.g., oligonucleotides with a poly-G tail such as, for example, D-type oligodeoxynucleotides with a poly-G tail.

The following examples further illustrate the invention but, of course, should not be construed as in any way limiting its scope.

EXAMPLE 1

This example demonstrates the synthesis of 2-(N-Formyl-N-methyl)aminoethan-1-ol.

2-(N-Formyl-N-methyl)aminoethan-1-ol is prepared from the reaction of 2-(methylamino)ethanol (available from Aldrich) with ethyl formate (Aldrich) as described in Grajkowski et al., *Org. Letters*, 3, 1287-1290 (2001).

EXAMPLE 2

Figure 2:
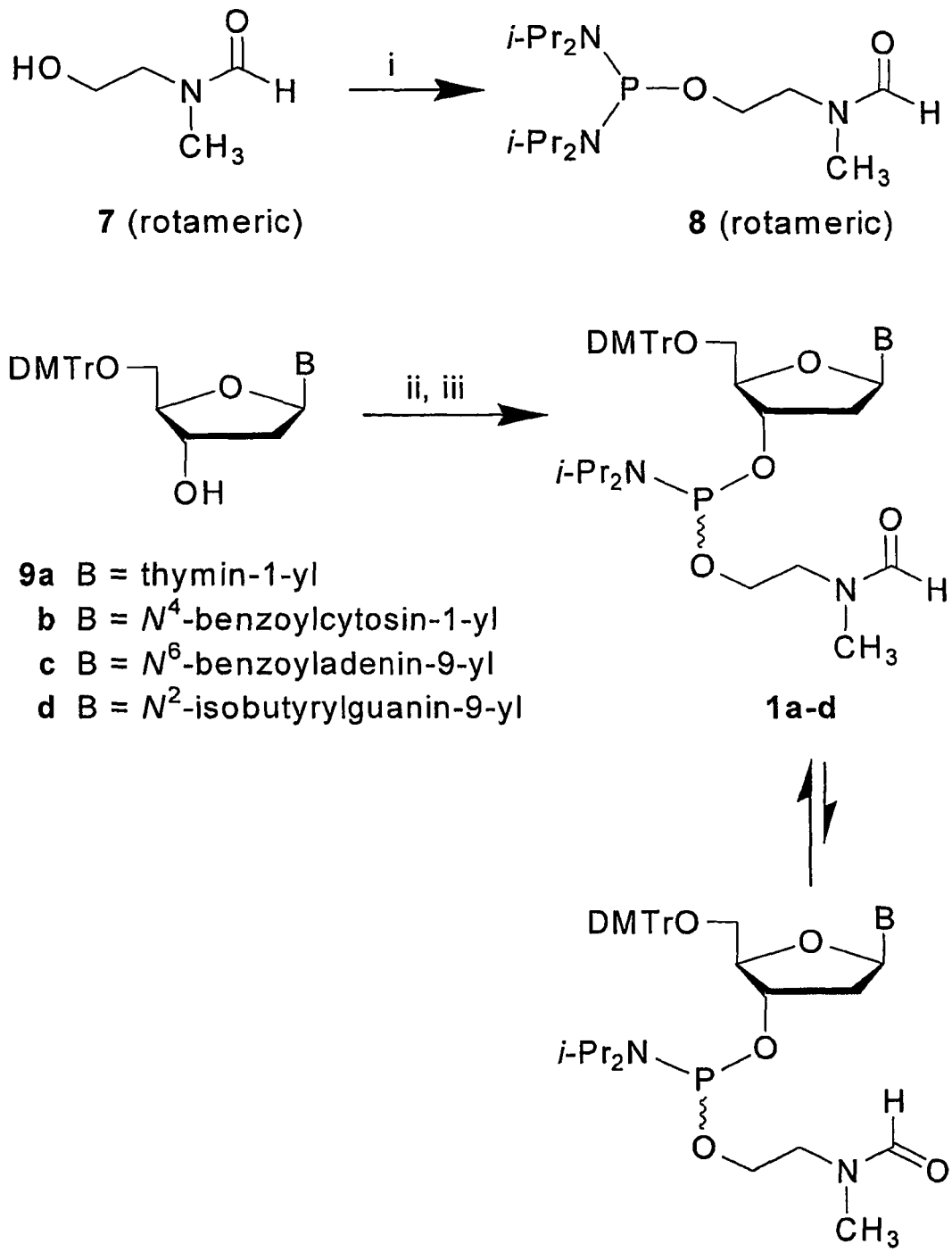
FIG. 2 illustrated the synthesis of deoxyribonucleoside phosphoramidite intermediates from suitably protected deoxyribonucleosides.

This example demonstrates the synthesis of N,N,N',N'-Tetraisopropyl-O-2-[(N-formyl-N-methyl)aminoethyl] phosphorodiamidite (See FIG. 2).

N,N,N',N'-Tetraisopropyl-O-2-[(N-formyl-N-methyl) aminoethyl]phosphorodiamidite is prepared following a procedure that has been modified from that reported earlier in Grajkowski et al., *Org. Letters*, 3, 1287-1290 (2001) and Wilk et al., *Deoxyribonucleoside phosphoramidites*, Current Protocols in Nucleic Acid Chemistry, John Wiley & Sons, Inc., New York, Vol. I, pp. 2.7.1-2.7.12. (2001).

To a stirred solution of 2-(N-formyl-N-methyl)aminoethan-1-ol (3.50 g, 34.0 mmol) and N,N-diisopropylethylamine (35.0 mL, 201 mmol) in anhydrous dichloromethane (20 mL) is added, at 25° C., a solution of bis(N,N-diisopropylamino)chlorophosphine (Aldrich) (9.98 g, 37.4 mmol) in dry dichloromethane (10 mL).

FIG. 2 represents the synthesis of phosphinylating reagent 8 and preparation of the deoxyribonucleoside phosphoramidites 1a-d (See FIG. 1) from suitably protected deoxyribonucleosides (9a-d). (i) bis(N,N-disopropylamino)chlorophosphine, N,N-diisopropylethylamine, $CH_2Cl_2$, 25° C., 2 h; (ii) 8, 1H-tetrazole, MeCN, 25° C., 2-16 h; (iii) silica gel chromatography.

Formation of the phosphorodiamidite is monitored by $^{31}P$ NMR spectroscopy, which reveals over a period of two hours, complete conversion of bis(N,N-diisopropylamino) chlorophosphine ($\delta_P$ 135.5 ppm) to two signals corresponding to the phosphinylating reagent as a mixture of rotamers ($\delta_P$ 118.0 and 118.7 ppm). The suspension is filtered and the filtrate is evaporated under reduced pressure to an oil. The material is transferred to a 50 mL round bottom flask, which is then connected to a vacuum jacketed short path distilling head and a distributing adapter. Vacuum distillation is performed using a heat gun to enable rapid heating with minimal decomposition. A colorless distillate (bp 145° C. at 1 mmHg) is obtained in 67% yield (7.58 g, 22.8 mmol). $^1$H NMR (300 MHz, $C_6D_6$): δ 3.56 (m, 2H), 3.53 (sept, J=6.9 Hz, 2H), 3.49 (sept, J=6.9 Hz, 2H), 2.30 (m, 2H), 1.80 (s, 3H), 1.63 (m, 4H), 1.23 (d, J=6.9 Hz, 12H), 1.19 (d, J=6.9 Hz, 12H). $^{13}$C NMR (75 MHz, $C_6D_6$): δ 15.2, 24.0, 24.1, 24.7, 24.8, 26.2, 31.1 (d, $J_{PC}$=9.6 Hz), 34.2, 44.6, 44.7, 64.1 (d, $^2J_{PC}$=21.5 Hz). $^{31}$P NMR (121 MHz, $C_6D_6$): δ 118.0, 118.7. EI-HRMS: calcd for $C_{16}H_{36}N_3O_2P$ (M$^+$) 333.2545, found 333.2528.

EXAMPLE 3

Figure 1:
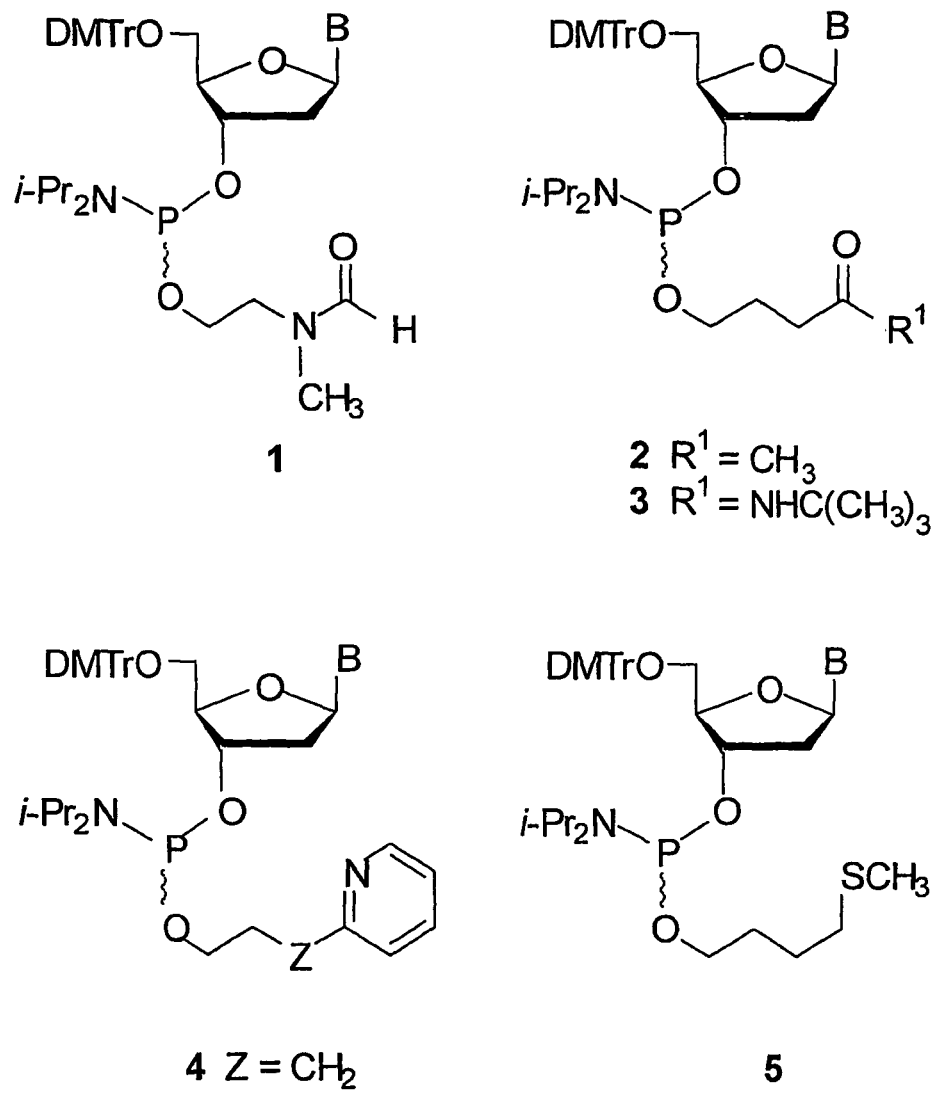
FIG. 1 illustrates the structures of deoxyribonucleoside phosphoramidite intermediates useful for preparing exemplary CpG oligonucleotide prodrugs of the present invention.

This example demonstrates a general procedure for the preparation of the deoxyribonucleoside phosphoramidites correlating to the nucleotide bases adenine, thymine, guanine, and cytosine (See FIGS. 1 and 2).

A properly protected deoxyribonucleoside (2 mmol) is dried under high vacuum for 4 hours in a 50 mL round-bottom flask and, then, dissolved in anhydrous MeCN (10 mL). To this solution is added N,N,N',N'-tetraisopropyl-O-2-[(N-formyl-N-methyl)aminoethyl]phosphorodiamidite (730 mg, 2.2 mmol) followed by 0.45 M 1H-tetrazole in MeCN (4.4 mL, 2 mmol), dropwise, over a period of 0.5 hours. Phosphinylation of suitably protected 2'-deoxyribonucleosides is usually complete within 2 hours at 25° C. with the exception of protected 2'-deoxyguanosine, which is allowed to proceed overnight. The reaction mixture is then concentrated under reduced pressure, dissolved in benzene:triethylamine (9:1 v/v), and chromatographed using a column (4 cm×10 cm) containing silica gel 60 (230-400 mesh, ~20 g) equilibrated in benzene:triethylamine (9:1 v/v).

The crude phosphoramidites are purified by silica gel chromatography using an eluent containing triethylamine to prevent dedimethoxytritylation and hydrolysis of the phosphoramidite monomers caused by the inherent acidity of silica gel. It is therefore critically important to remove excess triethylamine from the purified phosphoramidites monomers to avoid poor coupling efficiency during solid-phase oligonucleotide synthesis as a consequence of the neutralization of 1H-tetrazole during the activation step. The phosphoramidites are eluted from the column using the equilibration solvent as the eluent. Appropriate fractions are pooled, concentrated, and each of the deoxyribonucleoside phosphoramidites is obtained as a white foamy material.

The purified product is dissolved in ~3 mL of benzene and the solution is added to ~100 mL of cold (−20° C.) vigorously stirred hexane. The suspension is allowed to settle and most of the supernatant is carefully decanted. The wet material is pulverized under reduced pressure, and then dissolved in ~10 mL of benzene. The solution is frozen in a dry-ice/acetone bath, and lyophilized under high vacuum affording triethylamine-free phosphoramidites as white amorphous solids in yields ranging from 70-85%.

Characterization

5'-O-(4,4'-dimethoxytrityl)-3'-O—(N,N-diisopropylamino)[2-(N-formyl-N-methyl)aminoethoxy]phosphinyl-2'-deoxythymidine. $^{31}$P NMR (121 MHz, $C_6D_6$): δ 148.4, 148.3, 148.2. FAB-HRMS: calculated for $C_{41}H_{53}N_4O_9P$ (M+Cs)$^+$ 909.2604, found 909.2544.

$N^4$-benzoyl-5'-O—(4,4'-dimethoxytrityl)-3'-O—(N,N-diisopropylamino)[2-(N-formyl-N-methyl)aminoethoxy]phosphinyl-2'-deoxycytidine. $^{31}$P NMR (121 MHz, $C_6D_6$): δ 149.0, 148.9, 148.5, 148.4. FAB-HRMS: calculated for $C_{47}H_{56}N_5O_9P$ (M+Na)$^+$ 888.3714, found 888.3745.

$N^6$-benzoyl-5'-O-(4,4'-dimethoxytrityl)-3'-O—(N,N-diisopropylamino)[2-(N-formyl-N-methyl)aminoethoxy]phosphinyl-2'-deoxyadenosine. $^{31}$P NMR (121 MHz, $C_6D_6$): δ 148.9, 148.8, 148.1. FAB-HRMS: calculated for $C_{48}H_{56}N_7O_8P$ (M+Na)$^+$ 912.3827, found 912.3843.

$N^2$-isobutyryl-5'-O-(4,4'-dimethoxytrityl)-3'-O—(N,N-diisopropylamino)[2-(N-formyl-N-methyl)aminoethoxy]phosphinyl-2'-deoxyguanosine. $^{31}$P NMR (121 MHz, $C_6D_6$): δ 149.0, 143.9, 143.7. FAB-HRMS: calculated for $C_{45}H_{58}N_7O_9P$ (M+Na)$^+$ is 894.3933, found 894.3978.

Proton-decoupled $^{31}$P NMR spectra were recorded at 7.05 T (300 MHz for $^1$H) using deuterated solvents and 85% phosphoric acid in deuterium oxide as an external reference. The NMR spectrometer was run at 25° C. and chemical shifts δ are reported in parts per million (ppm).

Low- and high-resolution FAB mass spectra were acquired from samples dissolved in either 4-nitrobenzyl alcohol or a mixture of dithiothreitol and dithioerythritol (3:1, v/v) and bombarded with 8 keV fast cesium ions. A mass calibration standard of cesium iodide, or a mixture of cesium iodide and sodium iodide, was used. Accurate mass measurements were performed on [M+H]$^+$ or on [M+Na]$^+$ ions, which were obtained by addition of aqueous sodium iodide to the sample matrix.

EXAMPLE 4

This example demonstrates solid-phase oligonucleotide synthesis.

Solid phase synthesis of d[$G_{PS(FMA)}C_{PS(FMA)}T_{PS(FMA)}$ $A_{PS(FMA)}G_{PS(FMA)}A_{PS(FMA)}C_{PS(FMA)}G_{PS(FMA)}T_{PS(FMA)}$ $T_{PS(FMA)}A_{PS(FMA)}G_{PS(FMA)}C_{PS(FMA)}G_{PS(FMA)}T$] (CpG ODN fma 1555, where PS(fma) stands for a thermolytic 2-(N-formyl-N methyl)aminoethyl phosphorothioate triester function), and d[$G_{PS}C_{PS}T_{PS}A_{PS}G_{PS}A_{PS}C_{PS}G_{PS}T_{PS}T_{PS}A_{PS}$-$G_{PS}C_{PS}G_{PS}T$)](CpG ODN 1555, where PS stands for a phosphorothioate diester function) is performed on LCAA-CPG (1 μmol) using an ABI 392 DNA/RNA synthesizer and phosphoramidites 1a-d (FIG. 2) or commercial 2-cyanoethyl deoxyribonucleoside phosphoramidites as 0.1 M solutions in dry MeCN. The reaction time for each phosphoramidite coupling step is 180 seconds. With the exception of the deblocking solution, all other reagents that are necessary for the preparation of oligonucleotides were purchased and utilized as recommended by the instrument's manufacturer.

Given that only thioated oligodeoxyribonucleotides are prepared, the iodine oxidation step of the synthesis cycle is replaced with a sulfurization step employing 0.05 M 3H-1, 2-benzodithiol-3-one 1,1-dioxide in MeCN. The sulfurization step is performed before the capping step, and the reaction time for these steps is 120 seconds and 60 seconds, respectively. The dedimethoxytritylation step of the synthesis cycle is effected over a period of 60 seconds with a freshly prepared solution of 3% trichloroacetic acid (w/v) in dichloromethane. Upon completion of the last synthesis cycle, the terminal 5'-dimethoxytrityl group is not removed from the oligonucleotide to facilitate its separation from a population of shorter 5'-acetylated oligonucleotides that failed quantitative chain extension during oligonucleotide synthesis. The retention time ($t_R$) of CpG ODN fma 1555 is 37 min. under the chromatographic conditions used. The shape of the peak corresponding to the purified oligonucleotide is consistent with that of a complex mixture of rotameric diastereomers. See FIG. 4.

EXAMPLE 5

This example demonstrates oligonucleotide deprotection and purification.

The synthesis column containing the 5'-dimethoxytritylated oligonucleotide is placed into a stainless steel pressure vessel and exposed to pressurized ammonia (10 bar at 25° C.) for 12 hours. Upon release of excess ammonia from the pressure container, the 5'-dimethoxytritylated oligonucleotide is eluted off the column with 40% MeCN in 0.1 M triethylammonium acetate (TEAA, pH 7.0) (1 mL). The purification of each oligonucleotide is accomplished by reverse phase high performance liquid chromatography (RP-HPLC) using a semi-preparative 5-µm Supelcosil LC-18-S column (10 mm×25 cm) and the following elution gradient for 5'-O-DMTr-CpG ODN fma 1555: starting from 5% MeCN in 0.1 M TEAA (pH 7.0), 1.5% MeCN/min is pumped at a flow rate of 3 mL/min for 30 min. The following gradient is, however, used for the purification of 5'-O-DMTr-CpG ODN 1555: starting from 0.1 M TEAA (pH 7.0), 1% MeCN/min is pumped at a flow rate of 3 mL/min for 40 min. The product peaks are collected and then evaporated using a stream of air without heating. The residue is dissolved in 80% acetic acid (1 mL) and the solution is left standing at ambient temperature for 30 minutes. The acidic solution is evaporated also through the use of a stream of air without a heat source.

The oligonucleotide is then dissolved in a solution of 40% MeCN in 0.1 M TEAA (pH 7.0) (1 mL) and purified by RP-HPLC using the same conditions (column and elution gradient) as those employed for the purification of the respective 5'-O-DMTr-CpG ODN fma 1555 or 5'-O-DMTr-CpG ODN 1555. The pooling and evaporation of fractions containing the oligonucleotide is performed in a manner similar to that described for the respective 5'-O-DMTr-CpG ODN fma 1555 or 5'-O-DMTr-CpG ODN 1555. After reconstitution of the purified oligonucleotide in ddH$_2$O, its concentration was determined by UV spectrophotometry at 260 nm. The recovered yield of CpG ODN fma 1555 is 65 OD$_{260}$ units, whereas the recovered yield of CpG ODN 1555 is 95 OD$_{260}$ units. Each oligonucleotide is stored frozen at −20° C.

EXAMPLE 6

This example demonstrates oligonucleotide characterization.

The purity of CpG ODN fma 1555 and CpG ODN 1555 is assessed by RP-HPLC with an analytical 5 µm Supelcosil LC-18S column (4.6 mm×25 cm) according to the following conditions: starting from 0.1 M TEAA (pH 7.0), a linear gradient of 1% MeCN/min is pumped at a flow rate of 1 mL/min for 40 min. RP-HPLC profiles of the purified oligonucleotides are shown in FIG. 4.

Figure 4:
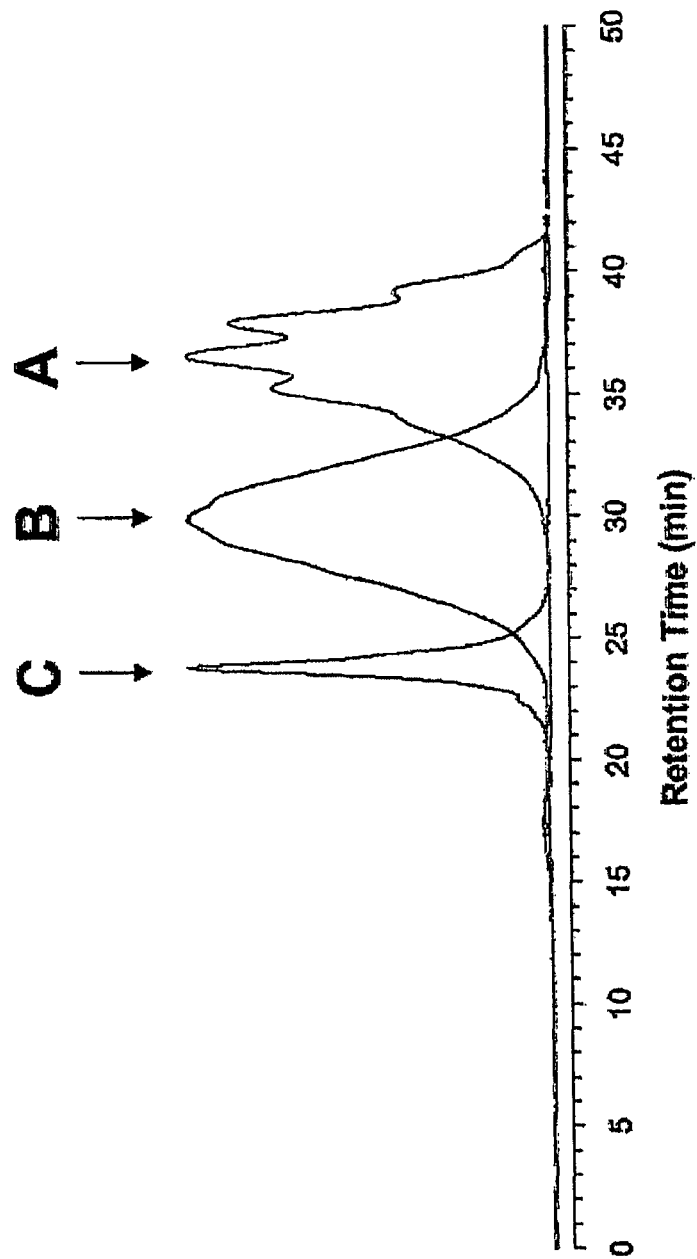
FIG. 4 is a RP-HPLC profile of an exemplary CpG oligonucleotide prodrug of the present invention.

FIG. 4 represents RP-HPLC profiles of d[G$_{PS(FMA)}$C$_{PS(FMA)}$T$_{PS(FMA)}$A$_{PS(FMA)}$G$_{PS(FMA)}$A$_{PS(FMA)}$C$_{PS(FMA)}$G$_{PS(FMA)}$T$_{PS(FMA}$T$_{PS(FMA)}$A$_{PS(FMA)}$G$_{PS(FMA)}$C$_{PS(FMA)}$G$_{PS(FMA)}$T] (CpG ODN fma1555). Curve A of FIG. 4 represents the chromatographic profile of purified CpG ODN fma1555. Curve B of FIG. 4 represents the chromatographic profile of purified CpG ODN fma1555 that was heated in 1×PBS buffer (pH 7.2) at 37° C. for 73 h (t$_{1/2}$). Curve C of FIG. 4 corresponds to the parent oligonucleotide (CpG ODN 1555) and represents the chromatographic profile of purified CpG ODN fma1555 that was heated in 1×PBS buffer (pH 7.2) for 626 h at 37° C. (or for 3 h at 90° C.). RP-HPLC analyses were performed using a 5 µm Supelcosil LC-18S column (4.6 mm×25 cm) according to the following conditions: starting from 0.1 M TEAA (pH 7.0), a linear gradient of 1% MeCN/min is pumped at a flow rate of 1 mL/min for 40 min. Peak heights of each profile are normalized to the highest peak, which is set to one arbitrary unit.

Purified CpG ODN fma 1555 (1 OD$_{260}$ unit each) is dissolved in 1×PBS buffer (pH 7.2) (0.5 mL) and placed in a heat block, pre-heated to 37±2° C. (or 90±2° C.), to thermolytically cleave the 2-(N-formyl-N-methyl)aminoethyl thiophosphate protecting group from the oligonucleotide. The half-time of thiophosphate deprotection was estimated to be 73 hours at 37° C. or 20 minutes at 90° C., and complete deprotection was achieved within 600 hours (or 3 hours at 90° C.). Fully deprotected CpG ODN fma1555 exhibited a t$_R$ (23 minutes) identical to that of CpG ODN 1555 under identical chromatographic conditions (FIG. 4, curve C). The thermolytic deprotection mechanism presumably proceeds through a cyclodeesterification mechanism (FIG. 3) that is typically observed with many of the thermosensitive phosphate/thiophosphate protecting groups investigated to date.

FIG. 3 is a theoretical representation of a mechanism for the thermolytic cleavage of 2-(N-formyl-N-methyl)aminoethyl thiophosphate protecting groups from CpG ODN fma1555. (i) NH$_3$ gas (~10 bar), 12 h, 25° C.; (ii) 0.1 M TEAA (pH 7.0) or 1×PBS buffer (pH 7.2), 90° C., 3 hours.

Figure 5:
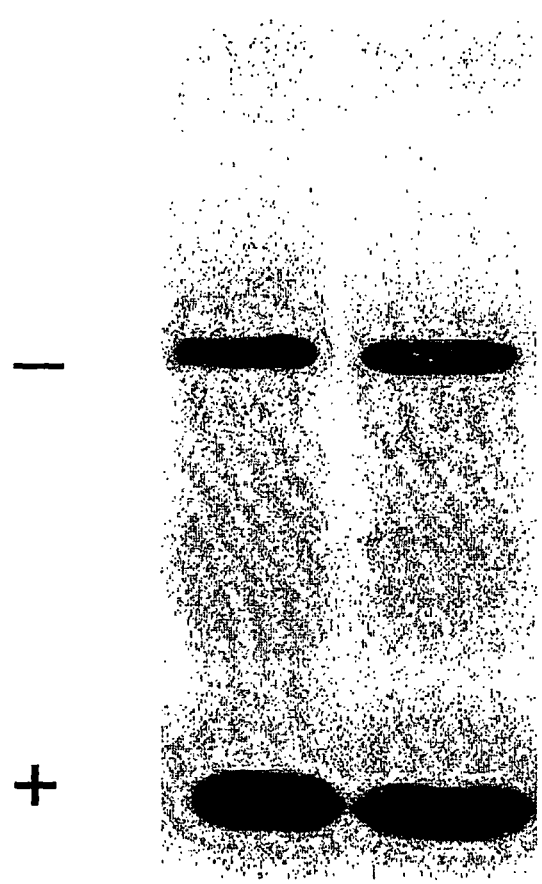
FIG. 5 is a representation of a polyacrylamide gel electrophoresis analysis of comparative fully deprotected oligonucleotide phosphorothioates under denaturing conditions.

Each fully deprotected oligonucleotide (0.25 OD$_{260}$ unit) was further analyzed by polyacrylamide gel electrophoresis (PAGE) using a 20% polyacrylamide-7 M urea gel (40 cm×20 cm×0.75 mm). The gel was prepared, as described in Maniatis, T., et al. *Molecular Cloning: A Laboratory Manual*, Cold Spring Harbor Laboratory Press, Cold Spring Harbor, N.Y., 173-185 (1982), using electrophoresis purity reagents. The gel was electorphoresed at 350 V until the bromophenol blue dye of the loading buffer travels ~80% of the length of the gel. The gel was then stained by soaking in a solution of Stains-all, as reported in Wilk, A., et al. *The 4-[N-methyl-N-(2,2,2-trifluoroacetyl)amino]butyl group as an alternative to the 2-cyanoethyl group for phosphate protection in the synthesis of oligodeoxyribonucleotides*, J. Org. Chem., 64, 7515-7522 (1999). A photograph of the gel is shown in FIG. 5. Each of the fully deprotected CpG ODN fma 1555 and CpG ODN 1555 migrated on the gel as a homogenous band with the same relative mobility, thus indicating an identical size. A photograph of the stained gel is shown in FIG. 5.

FIG. 5 is a photograph of a polyacrylamide gel electrophoresis analysis of fully deprotected and RP-HPLC-purified oligonucleoside phosphorothioates under denaturing conditions (7 M urea, 1×TBE buffer, pH 8.3). Left lane: CpG ODN 1555 synthesized from commercial 2-cyanoethyl deoxyribonucleoside phosphoramidites and deprotected by treatment with pressurized ammonia gas (~10 bar) for 12 h at 25° C. Right lane: CpG ODN fma1555 synthesized from phosphoramidites 1a-d and deprotected by treatment pressurized ammonia gas (~10 bar) for 12 h at 25° C. followed by heating in 1×PBS buffer (pH 7.2) for 626 h at 37° C. (or for 3 h at 90° C.). Oligonucleotides are visualized as purple bands upon staining the gel with Stains-all. Bromophenol blue is used as a marker and shows as a large band, in each lane, at the bottom of the gel.

The purified oligodeoxyribonucleoside phosphorothioates were also characterized by Positive ion Electrospray ionization Time of Flight Mass Spectrometry. CpG ODN fma 1555

(+ESI-TOF MS): calculated for $C_{203}H_{283}N_{71}O_{89}P_{14}S_{14}$ [M]$^+$6024, found 6023. CpG ODN 1555 (+ESI-TOF MS): calculated for $C_{147}H_{185}N_{57}O_{75}P_{14}S_{14}$ [M+14H]$^+$ 4832, found 4832.

Both purified CpG ODN fma 1555 and CpG ODN 1555 were assayed for endotoxins using the Limulus amebocyte lysate assay and were found to contain <0.1 endotoxin unit per mg of oligonucleotide.

EXAMPLE 7

This example demonstrates the biological activity of an exemplary thermolytic CpG-containing DNA oligonucleotide on eliciting a protective immune response in mice infected with an intracellular pathogen. In particular, the immunostimulatory properties of CpG ODN fma 1555 were evaluated in mice and compared with that of the parent oligonucleotide, CpG ODN 1555, which is known for its immunoprotective properties.

Balb/C mice were obtained from the National Cancer Institute (Frederick, Md.), housed in sterile microisolator cages in the CBER specific-pathogen free animal facility, and bred at 6-12 weeks of age. All experiments were approved by the CDER and CBER Animal Care and Use Committee.

Protocol A: Previous studies have shown that administration of CpG-containing DNA oligonucleotides alone reduced the severity of a *L. major* challenge. To assess whether mice treated with CpG ODN fma 1555 acts like parent molecule CpG ODN 1555 to stimulate the innate immune system to protect mice from a *L. major* infection, adult female Balb/c mice (6-12 weeks old) were challenged with 1000 metacyclic promastigotes intradermally in the ear and left either untreated or treated in situ with CpG ODN fma 1555 or CpG ODN 1555. *Leishmania major* infections were performed as described in Mendez et al., *Infect. & Immun.*, 71, 5121-5129 (2003). *L. major* clone VI (MHOM/IL/80/Friedlin) Promastigotes were grown at 26° C. in medium 199 supplemented with 20% Hi-FCE (HyClone), 100-U penicillin/mL, 100 μg of streptomycin/mL, 2 mM L-glutamine, 40 mM HEPES, 0.1 mM adenine in 50 mM HEPES, 5 mg of hemin/mL of 50% triethanolamine, and 1 mg of 6-biotin (M199/S)/mL. Infective-stage promastigotes (metacyclics) of *L. major* were isolated from stationary cultures (4 to 5 days old) by negative selection of infective forms using peanut agglutinin (Vector Laboratories). Susceptible Balb/c mice (6-10 weeks of age, 4/group) were infected in the ear dermis by using a 27.5-gauge needle and a total volume of 5 μL. Cutaneous inoculation of live metacyclic *L. major* parasites causes a cutaneous lesion that resembles those observed in human cutaneous leishmaniasis. Treated animals received 25 μg of CpG ODN fma 1555 or CpG ODN 1555 in situ. The number of parasites and total volume was maintained constant for all animals. Cutaneous inoculation of live metacyclic *L. major* parasites causes a cutaneous lesion that resembles those observed in human cutaneous leishmaniasis. The size of the cutaneous lesion was monitored weekly. No obvious weight loss was observed in uninfected mice treated with the oligonucleotides.

Figure 6:
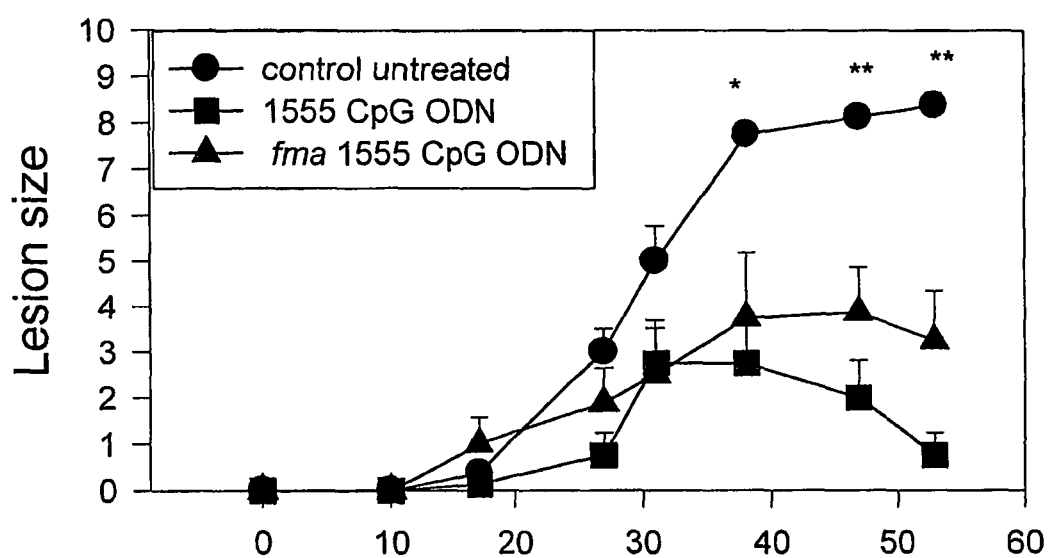
FIG. 6 depicts the results of a study demonstrating the in vivo immunoprotection against progressive *Leishmania major* infection in mice treated with an exemplary CpG oligonucleotide prodrug of the present invention.

FIG. 6 is a graphical representation of immunoprotection of mice treated with CpG ODN fma 1555 against progressive *Leishmania major* infection. Balb/c mice (4 mice/group) were challenged in the ear with 10$^3$ live *Leishmania major* metacyclic promastigotes. Control ODN were either left untreated or treated locally (ID) with CpG ODN 1555. As previously reported, untreated Balb/c mice developed an ulcerative skin lesion that ultimately led to the loss of the outer ear 10 weeks after infection. In contrast, Balb/c mice that were treated with CpG ODN fma 1555 or CpG ODN 1555 showed a striking reduction in dermal pathology compared with that of untreated mice. Although the lesions tended to be smaller in the CpG ODN 1555-treated mice than in the CpG ODN fma 1555-treated mice (FIG. 6), the difference was not statistically significant. Statistical analysis was performed by ANOVA *=p<0.05, **=p<0.01. These results demonstrate that thermolytic CpG-containing DNA oligonucleotides have biological efficacy and can elicit a protective immune response in mice infected with an intracellular pathogen.

Protocol B: Since the thermolytic deprotection of CpG-ODN fma 1555 has a half-time of 73 hours at 37° C., the effects of the oligonucleotide should be delayed relative to that of CpG ODN 1555. The delay in immunoprotective activity of CpG ODN fma 1555 was assessed using a model of Tacaribe virus infection in newborn Balb/c mice. Previous studies had shown that CpG-containing DNA oligonucleotides can protect newborn mice from death only when these are administered at the time, or up to 3 days after infection (manuscript in preparation).

Figure 7:
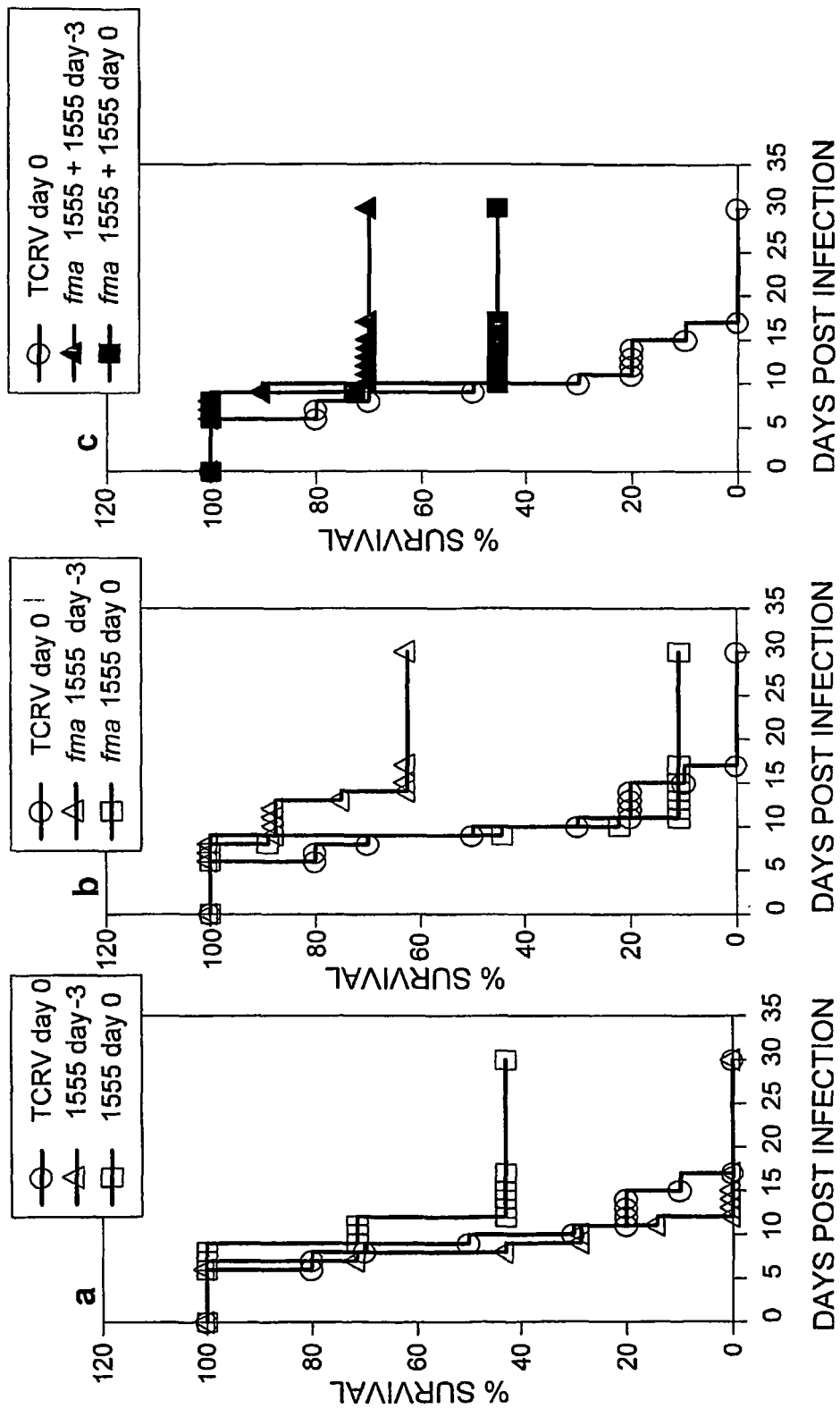
FIG. 7 graphically depicts the survival of TCRV-infected mice treated with an exemplary CpG oligonucleotide prodrug of the present invention.

Neonatal BALB/c mice were bred in house under specific pathogen free conditions. Newborn mice were infected intraperitoneally with Tacaribe virus (2000 TC$_{50}$/animal) 1 to 4 days after birth. Mice were left untreated or treated with CpG ODN fma 1555 and/or CpG ODN 1555 on the day of infection or 3 days before infection. The mice were monitored daily but infections were allowed to proceed to their natural outcome in order to assess survival. Survival for each condition was determined from 24 independent experiments using 2-4 mice per group. No obvious delay in development or weight loss was observed in uninfected mice treated with the oligonucleotides. (See FIG. 7).

FIGS. 7A-7C are graphical representations of the survival of TCRV-infected mice treated with CpG ODN fma 1555. Newborn Balb/c mice (1-4 days old) were infected with Tacaribe virus (2000 TC$_{50}$/mouse), a New world arena virus that causes a lethal meningoencephalitis in newborn mice (100% lethal). The data depicted in FIG. 7A demonstrates that CpG ODN 1555 (25 μg/mouse IP) protects newborn mice from infection (43% survival) when administered at the time of infection (open square), but is ineffective when administered 3 days prior to infection (open triangle). The data depicted in FIG. 7B demonstrates that CpG ODN fma 1555 (25 μg/mouse) protected mice (63% survival) when administered 3 days prior to infection (open triangle), but not when administered at the time of infection (open square). The data depicted in FIG. 7C demonstrates that the combination of CpG ODN 1555 and CpG fma 1555 extends the period of protection from infection (filled triangle).

These findings are consistent with the theory that CpG ODN fma 1555 is behaving as a prodrug. Interestingly, when CpG ODN fma 1555 and CpG ODN 1555 were co-administered, the survival rate reached 60-70% regardless of whether administration of the oligonucleotides was performed on the same day, or 3 days prior to Tacaribe virus infection. Hence the data further suggest that the combination of CpG ODN 1555 and CpG ODN fma 1555 widened the therapeutic window.

EXAMPLE 8

This example demonstrates the production of interferon-α from PBMC from four normal donors that were cultured in the presence of conventional D35, or D35 protected with thermolabile moieties for 72 hours.

PBMC from four normal donors were cultured in the presence of conventional D35 or D35 protected with thermolabile moieties for 72 hours. Supernatants from these cells were tested for production of interferon-α. As shown in the table below, D ODN with mixed backbones (D35, phosphodiester backbone for the motif and flanking regions and phosphorothioate on the 2-5 bases on the 3' end to protect from nucleases) induced interferon-α. ODNs that had the poly-G tail protected with thermolabile groups (fma poly-G tail D35) induced similar plasmacytoid dendritic cell activation as assessed by the interferon-α secreted. Neither D35 with a PS backbone nor control ODNs lacking the CpG motif induced interferon-α secretion regardless of the presence or absence of the thermolabile groups indicating that the thermolabile moieties do not induce pDC activation.

Interferon-A Secreted in Response to Stimulation with CpG ODN Type-D

|  | Donor 1 | Donor 2 |
|---|---|---|
| Media | 0.5 | 0.5 |
| D19 | 9.9 | 11.7 |
| D35 | 12.8 | 14.5 |
| D144 | 0.5 | 0.5 |
| fma poly G tail D35 | 11.3 | 11.5 |
| fma poly G tail D144 | 0.5 | 0.5 |
| fma D35 | 0.5 | 0.5 |
| fma D144 | 0.5 | 0.5 |

The sequences for the ODNs tested are as follows:

```
D35                       ggTGCATCGATGCAGGGGgg fma D35                   g*g*T*G*C*A*T*C*G*A*T*G*C*A*G*G*G*g*g partial fma D35           g*g*T*G*CATCGATG*C*A*G*G*G*g*g fma poly-G tail D35       ggTGCATCGATGCAG*G*G*g*g partial fma poly-G tail D35  ggTGCATCGATGCA*GG*GG*gg fma PS D35                g*g*t*g*catcgatg*c*a*g*g*g*g*g D144                      ggTGCATTGATGCAGGGGgg  (No GpG motif)

partial fma D144          g*g*T*G*C*ATTGAT*G*C*A*G*G*G*g*g fma poly-G tail D144      ggTGCATTGATGCAG*G*G*g*g
```

*= Thermolabile group; upper case letters = phosphodiester bases; lower case letters = phosphorothioate bases.

EXAMPLE 9

This example demonstrates the effect of single ID administration of thermolabile CpG DNA type-D on the severity of cutaneous leishmaniasis in Rhesus macaques.

Figure 10C:
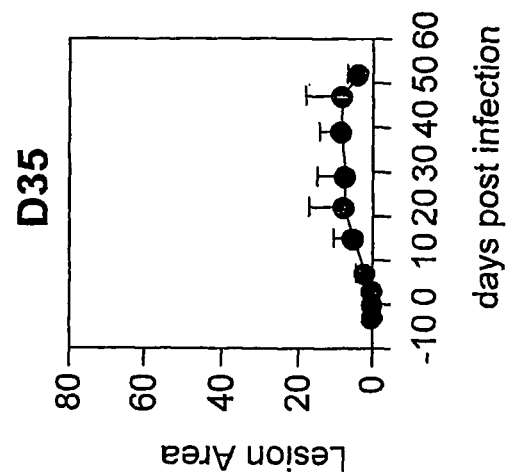
FIG. 10 depicts the results of a study demonstrating the in vivo immunoprotection against cutaneous leishmaniasis in monkeys treated with an exemplary CpG oligonucleotide prodrug of the present invention.
Figure 10B:
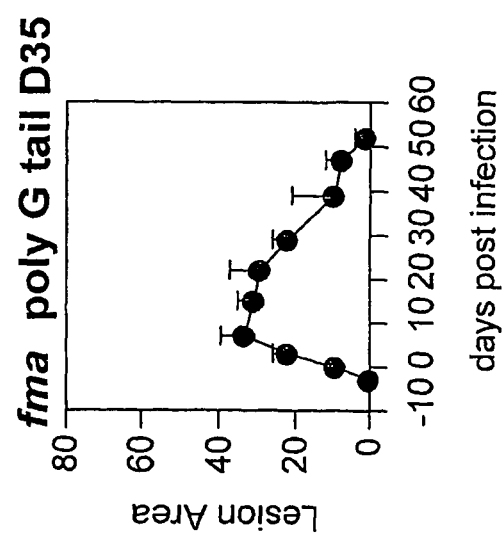
Figure 10A:
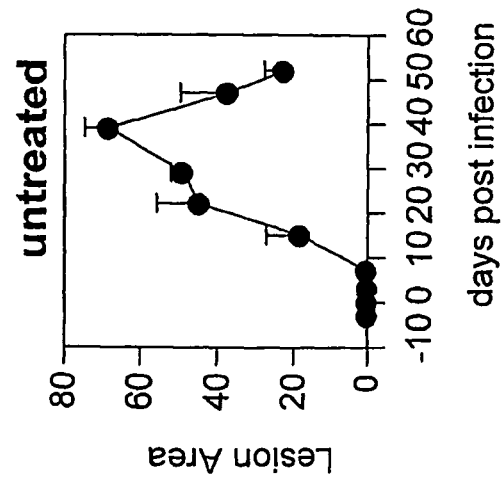

Rhesus macaques (3-6/group) were challenged with $3\times10^7$ L. Major metacyclic promastigotes ID on the forehead and treated with CpG ODN type-D (sequence D35, 500 μg/macaque) (See Example 8) that had five thermolabile-protected bases on the poly-G tail. Macaques treated with CpG ODN type-D (500 μg/macaque) or untreated served as positive and negative controls, respectively. The severity of the lesions was assessed weekly. The results are depicted graphically in FIGS. 10A, 10B, and 10C. The thermolabile protected CpG ODNs reduced the severity of the lesions.

EXAMPLE 10

This example demonstrates the effect of thermolabile substituents on tetrad formation.

The presence of tetrads in sample solutions was monitored by CD spectra. All samples (1.5 OD) were dissolved in 100 μl of water. Two aliquots of 33 μl (0.5 OD) of each stock was diluted simultaneously to 300 μl of 10 mM Tris-Ci, pH. 7.5 or 10 mM Tris-Cl, pH. 7.5 plus 100 mM KCl. CD spectra were recorded in 0.5 nm steps between 230 nm and 320 nm, with 2 nm band wind and 5 s integration time. For each spectrum, the baseline was recorded using the same conditions and subtracted afterwards using Kaleida-Graph. All measurements were performed at 25 degrees C. in a cell with a 2 mm path length and repeated after 24 h (samples kept at 4° C.). The results are shown below in Table 1.

TABLE 1

| Name | Sequence | Wavelength (nm) | Tetraplex Formation |
| --- | --- | --- | --- |
| D35 (comparative) | ggTGCATCGATGCAGGGGgg | 265 | Yes |
| fma D35 (invention) | g*g*T*G*C*A*T*C*G*A*T*G*C*A*G*G*G*g*g | 280 | No |
| partial fma D35 (invention) | g*g*T*G*CATCGATG*C*A*G*G*G*g*g | 280 | No |
| fma G tail D35 (invention) | ggTGCATCGATGCAG*G*G*g*g | 280 | No |
| partial fma G tail D35 (invention) | ggTGCATCGATGCA*GG*GG*gg | 270 | Yes |
| Control sequence | ggTGCATCGATGCATGTGtg | 280 | No |

The foregoing data demonstrate that tetrad formation can be avoided in CpG oligonucleotides that have a tendency to form tetrads by functionalizing the oligonucleotide with one or more thermolabile substituents in accordance with the present invention. The use of thermolabile substituents can reduce the formation of tetrads in D-type or A-type CpG ODNs, as well as other ODNs that make G-tetrads.

All references, including publications, patent applications, and patents, cited herein are hereby incorporated by reference to the same extent as if each reference were individually and specifically indicated to be incorporated by reference and were set forth in its entirety herein.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A CpG oligonucleotide prodrug comprising a CpG oligonucleotide that has a poly-G tail at the 3'-end of the oligonucleotide and a thermolabile substituent bonded thereto, wherein the thermolabile substituent is bonded to the non-bridging oxygen atom of a deoxyguanosine phosphate, phosphorothioate, or phosphoroselenoate diester present in the poly-G tail in an amount sufficient to inhibit G-tetrad formation, wherein the CpG oligonucleotide that has a poly-G tail forms a tetraplex in the absence of the thermolabile substituent, and, wherein the thermolabile substituent is of the formula:

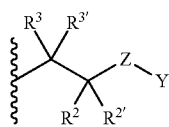
(I)

wherein:
R², R²', R³ and R³'are the same or different and each is H, an alkyl, an alkenyl, an alkynyl, a cycloalkyl, an aryl, or an aralkyl, or R² or R²', in combination with R³ or R³', together with the carbon atoms to which they are bonded, comprise a cyclic substituent of the formula:

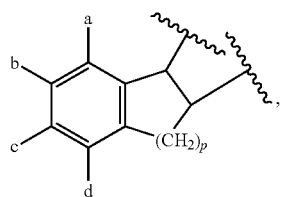

wherein p is an integer from 0-6 and a-d are the same or different and each is selected from the group consisting of H, an alkyl, a nitro, a dialkylamino, an alkoxy, an alkylthio, a cyano and a halogen;
Z is O, S, $NR^{4a}$, $CR^{4a}R^{4a'}$ or $CR^{4a}R^{4a'}CR^{4b}R^{4b'}$, wherein $R^{4a}$, $R^{4a'}$, $R^{4b}$ and $R^{4b'}$ are the same or different and each is H, an alkyl, an alkenyl, an alkynyl, a cycloalkyl, an aryl, or an aralkyl; and
Y is $CH_2R^1$ or $C(X)H$ wherein X is O or S, and $R^1$ is H, $R^{1a}$, $OR^{1a}$, $SR^{1a}$ or $NR^{1a}R^{1a'}$, wherein $R^{1a}$ and $R^{1a'}$ are the same or different and each is H, an alkyl, an alkenyl, an alkynyl, a cycloalkyl, an aryl, or an aralkyl;
wherein $R^{1a}$, $R^{1a'}$, $R^2$, $R^{2'}$, $R^3$, $R^{3'}$, $R^{4a}$, $R^{4a'}$, $R^{4b}$ and $R^{4b'}$ are unsubstituted or substituted with one or more substituents, which are the same or different, selected from the group consisting of $OR^5$, $SR^5$, CN, $NO_2$, $N_3$, and a halogen, wherein $R^5$ is H or an alkyl.

2. The CpG oligonucleotide prodrug of claim 1, wherein R², R²', R³ and R³'are all hydrogen.

3. The CpG oligonucleotide prodrug of claim 1, wherein Z is $CR^{4a}R^{4a'}$ or $CR^{4a}R^{4a'}CR^{4b}R^{4b'}$ and $R^{4a}$, $R^{4a'}$, $R^{4b}$ and $R^{4b'}$ are all hydrogen.

4. The CpG oligonucleotide prodrug of claim 1, wherein Z is $NR^{4a}$ and $R^{4a}$ is alkyl.

5. The CpG oligonucleotide prodrug of claim 1, wherein Y is $CH_2R^1$ or C(O)H and $R^1$ is H, OH, $R^{1a}$, $SR^{1a}$ or $NR^{1a}R^{1a'}$, wherein $R^{1a}$ is alkyl and $R^{1a'}$ is H.

6. The CpG oligonucleotide prodrug of claim 5, wherein $R^{1a}$ is methyl or tert-butyl.

7. The CpG oligonucleotide of claim 2, wherein the thermolabile substituent is selected from the group consisting of:

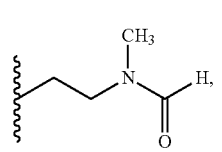 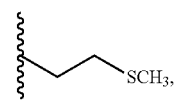

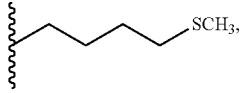

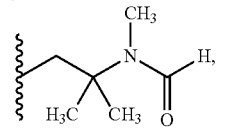 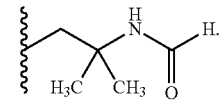

8. The CpG oligonucleotide prodrug of claim 7, wherein the thermolabile substituent is selected from the group consisting of:

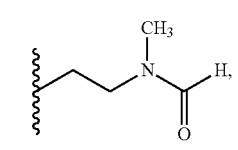

and

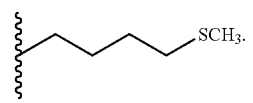

9. The CpG oligonucleotide prodrug of claim 1, comprising a K-type oligodeoxynucleotide sequence, a B-type oligodeoxynucleotide sequence, an A-type oligodeoxynucleotide sequence, or a D-type oligodeoxynucleotide sequence.

10. The CpG oligonucleotide prodrug of claim 7, comprising a K-type oligodeoxynucleotide sequence, a B-type oligodeoxynucleotide sequence, an A-type oligodeoxynucleotide sequence, or a D-type oligodeoxynucleotide sequence.

11. The CpG oligonucleotide prodrug of claim 1, wherein at least one nucleotide-of-the CpG oligonucleotide comprises a thermolabile phosphodiester protecting group.

12. The CpG oligonucleotide prodrug of claim 1, wherein the CpG oligonucleotide comprises the nucleic acid sequence of SEQ ID NO: 6, SEQ ID NO: 7, or SEQ ID NO: 8.

13. The CpG oligonucleotide prodrug of claim 1, wherein the CpG oligonucleotide induces cytokine production when the CpG oligonucleotide prodrug is administered to a human.

14. The CpG oligonucleotide prodrug of claim 1, wherein the CpG oligonucleotide induces cytokine production when the CpG oligonucleotide prodrug is administered to a mouse.

15. A pharmaceutical composition comprising a carrier and a therapeutically effective amount of at least one CpG oligonucleotide prodrug of claim 1.

16. A pharmaceutical composition comprising a carrier and a therapeutically effective amount of at least one CpG oligonucleotide prodrug of claim 7.

17. A pharmaceutical composition comprising a carrier and a therapeutically effective amount of at least one CpG oligonucleotide prodrug of claim 8.

18. The CpG oligonucleotide prodrug of claim 7, wherein at least one nucleotide of the CpG oliogonucleotide comprises a thermolabile phosphodiester protecting group.

19. A pharmaceutical composition comprising a carrier and a therapeutically effective amount of at least one CpG oligonucleotide prodrug of claim 2.

20. A pharmaceutical composition comprising a carrier and a therapeutically effective amount of at least one CpG oligonucleotide prodrug of claim 4.

21. A method of inducing production of a cytokine in a subject, comprising administering to the subject a therapeutically effective amount of the pharmaceutical composition of claim 15, thereby inducing production of the cytokine in the subject.

22. The method of claim 21, wherein the cytokine is interleukin (IL)-10, interferon (IFN)-α or IFN-γ.

23. The method of claim 21, wherein the cytokine is IL-6 or IFN-α.

24. The method of claim 21, wherein the GpG oligonucleotide comprises a K-type oligodeoxynucleotide sequence, a B-type oligodeoxynucleotide sequence, an A-type oligodeoxynucleotide sequence, or a D-type oligodeoxynucleotide sequence.

25. The method of claim 21, wherein the thermolabile substituent is selected from the group consisting of:

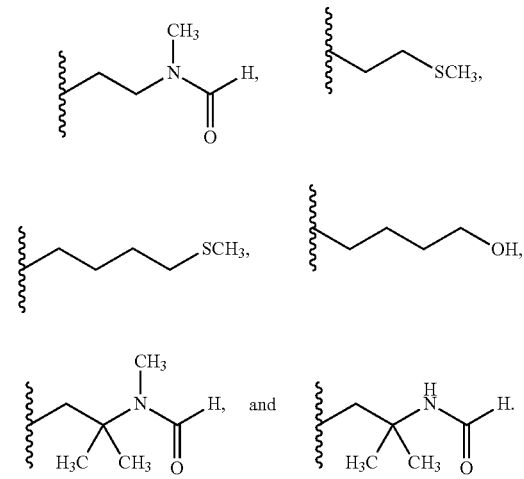

* * * * *

SEQUENCE LISTING

```
<160> NUMBER OF SEQ ID NOS: 14

<210> SEQ ID NO 1
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(14)
<223> OTHER INFORMATION: Nucleotide has phosphorothionate diester
      function

<400> SEQUENCE: 1
gctagacgtt agcgt                                                    15

<210> SEQ ID NO 2
<211> LENGTH: 15
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<222> LOCATION: (1)..(14)
<223> OTHER INFORMATION: Nucleotide has thermolytic 2-(N-formyl)-N
      methyl) aminoethyl phosphorothioate triester function

<400> SEQUENCE: 2
gctagacgtt agcgt                                                        15

<210> SEQ ID NO 3
<211> LENGTH: 10
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: "n" = any nucleotide.
<220> FEATURE:
<221> NAME/KEY: misc_feature
<222> LOCATION: (5)..(6)
<223> OTHER INFORMATION: unmethylated nucleotide
<220> FEATURE:
<221> NAME/KEY: misc_feature
<222> LOCATION: (8)..(10)
<223> OTHER INFORMATION: "n" = any nucleotide.

<400> SEQUENCE: 3 nnntcgwnnn                                                              10

<210> SEQ ID NO 4
<211> LENGTH: 14
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(5)
<223> OTHER INFORMATION: "n" = any nucleotide.
<220> FEATURE:
<221> NAME/KEY: misc_feature
<222> LOCATION: (8)..(9)
<223> OTHER INFORMATION: unmethylated nucleotide
<220> FEATURE:
<221> NAME/KEY: misc_feature
<222> LOCATION: (12)..(14)
<223> OTHER INFORMATION: "n" = any nucleotide.

<400> SEQUENCE: 4
ggnnnrycgr ynnn                                                         14

<210> SEQ ID NO 5
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (19)..(20)
<223> OTHER INFORMATION: Phosphorothioate base

<400> SEQUENCE: 5
ggtgcatcga tgcagggggg                                                   20
```

-continued

```
<210> SEQ ID NO 6
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (1)..(19)
<223> OTHER INFORMATION: Nucleotide has thermolabile group
<220> FEATURE:
<221> NAME/KEY: misc_feature
<222> LOCATION: (19)..(20)
<223> OTHER INFORMATION: Phosphorothioate base

<400> SEQUENCE: 6
ggtgcatcga tgcagggggg                                              20

<210> SEQ ID NO 7
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (1)..(4)
<223> OTHER INFORMATION: Nucleotide has thermolabile group
<220> FEATURE:
<221> NAME/KEY: misc_feature
<222> LOCATION: (12)..(19)
<223> OTHER INFORMATION: Nucleotide has thermolabile group
<220> FEATURE:
<221> NAME/KEY: misc_feature
<222> LOCATION: (19)..(20)
<223> OTHER INFORMATION: Phosphorothioate base

<400> SEQUENCE: 7
ggtgcatcga tgcagggggg                                              20

<210> SEQ ID NO 8
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (15)..(19)
<223> OTHER INFORMATION: Nucleotide has thermolabile group
<220> FEATURE:
<221> NAME/KEY: misc_feature
<222> LOCATION: (19)..(20)
<223> OTHER INFORMATION: Phosphorothioate base

<400> SEQUENCE: 8
ggtgcatcga tgcagggggg                                              20

<210> SEQ ID NO 9
<211> LENGTH: 20
```

```
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (14)..(14)
<223> OTHER INFORMATION: Nucleotide has thermolabile group
<220> FEATURE:
<221> NAME/KEY: misc_feature
<222> LOCATION: (16)..(16)
<223> OTHER INFORMATION: Nucleotide has thermolabile group
<220> FEATURE:
<221> NAME/KEY: misc_feature
<222> LOCATION: (18)..(18)
<223> OTHER INFORMATION: Nucleotide has thermolabile group
<220> FEATURE:
<221> NAME/KEY: misc_feature
<222> LOCATION: (19)..(20)
<223> OTHER INFORMATION: Phosphorothioate base

<400> SEQUENCE: 9
ggtgcatcga tgcagggggg                                               20

<210> SEQ ID NO 10
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Phosphorothioate base
<220> FEATURE:
<221> NAME/KEY: misc_feature
<222> LOCATION: (1)..(4)
<223> OTHER INFORMATION: Nucleotide has thermolabile group
<220> FEATURE:
<221> NAME/KEY: misc_feature
<222> LOCATION: (12)..(19)
<223> OTHER INFORMATION: Nucleotide has thermolabile group

<400> SEQUENCE: 10
ggtgcatcga tgcagggggg                                               20

<210> SEQ ID NO 11
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (19)..(20)
<223> OTHER INFORMATION: Phosphorothioate base

<400> SEQUENCE: 11
ggtgcattga tgcagggggg                                               20

<210> SEQ ID NO 12
<211> LENGTH: 20
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (1)..(5)
<223> OTHER INFORMATION: Nucleotide has thermolabile group
<220> FEATURE:
<221> NAME/KEY: misc_feature
<222> LOCATION: (11)..(19)
<223> OTHER INFORMATION: Nucleotide has thermolabile group
<220> FEATURE:
<221> NAME/KEY: misc_feature
<222> LOCATION: (19)..(20)
<223> OTHER INFORMATION: Phosphorothioate base

<400> SEQUENCE: 12
ggtgcattga tgcagggggg                                              20

<210> SEQ ID NO 13
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (15)..(19)
<223> OTHER INFORMATION: Nucleotide has thermolabile group
<220> FEATURE:
<221> NAME/KEY: misc_feature
<222> LOCATION: (19)..(20)
<223> OTHER INFORMATION: Phosphorothioate base

<400> SEQUENCE: 13
ggtgcattga tgcagggggg                                              20

<210> SEQ ID NO 14
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate base
<220> FEATURE:
<221> NAME/KEY: misc_feature
<222> LOCATION: (19)..(20)
<223> OTHER INFORMATION: Phosphorothioate base

<400> SEQUENCE: 14
ggtgcatcga tgcatgtgtg                                              20
```